(12) United States Patent
Davidson et al.

(10) Patent No.: US 11,168,091 B2
(45) Date of Patent: Nov. 9, 2021

(54) QUANTIFICATION AND PREPARATION OF PHARMACEUTICAL GRADE CANTHARIDIN

(71) Applicant: Verrica Pharmaceuticals Inc., West Chester, PA (US)

(72) Inventors: Matthew Davidson, San Carlos, CA (US); Garry Southan, Swampscott, MA (US); Steven R. Schow, Redwood City, CA (US); Robert Moore, Santa Rosa, CA (US)

(73) Assignee: Verrica Pharmaceuticals Inc., West Chester, PA (US)

( * ) Notice: Subject to any disclaimer, the term of this patent is extended or adjusted under 35 U.S.C. 154(b) by 48 days.

(21) Appl. No.: 15/544,669

(22) PCT Filed: Jan. 20, 2016

(86) PCT No.: PCT/US2016/014139
§ 371 (c)(1),
(2) Date: Jul. 19, 2017

(87) PCT Pub. No.: WO2016/118633
PCT Pub. Date: Jul. 28, 2016

(65) Prior Publication Data
US 2019/0031674 A1      Jan. 31, 2019

Related U.S. Application Data

(60) Provisional application No. 62/105,622, filed on Jan. 20, 2015.

(51) Int. Cl.
*G01N 21/00*    (2006.01)
*C07D 493/18*   (2006.01)
(Continued)

(52) U.S. Cl.
CPC .......... *C07D 493/18* (2013.01); *A61K 31/365* (2013.01); *G01N 21/33* (2013.01);
(Continued)

(58) Field of Classification Search
CPC .................................................. C07D 493/18
(Continued)

(56) References Cited

U.S. PATENT DOCUMENTS 4,148,874 A      4/1979   Smith
4,298,752 A     11/1981   Dauben et al.
(Continued)

FOREIGN PATENT DOCUMENTS

CN      1966508 A       5/2007
CN    101012230 A       8/2007
(Continued)

OTHER PUBLICATIONS

English Translation of CN101108853 access from Espacenet on Jun. 11, 2019 (Year: 2019).*
(Continued)

*Primary Examiner* — Christine T Mui
*Assistant Examiner* — Emily R. Berkeley
(74) *Attorney, Agent, or Firm* — Wolf, Greenfield & Sacks, P.C.

(57) ABSTRACT

The present disclosure provides methods for purifying a solution comprising cantharidin and cantharidin-associated impurities. A method to purify the solution can comprise recrystallization or sublimation, for example. The purified cantharidin can be analyzed using a detection method comprising a stationary phase and one or more mobile phases.

20 Claims, 11 Drawing Sheets

(51) Int. Cl.
  *G01N 21/33* (2006.01)
  *A61K 31/365* (2006.01)
  *G01N 30/74* (2006.01)
  *G01N 33/15* (2006.01)

(52) U.S. Cl.
  CPC .............. *G01N 30/74* (2013.01); *G01N 33/15* (2013.01); *C07B 2200/13* (2013.01)

(58) Field of Classification Search
  USPC .............................................. 422/82.9, 82.09
  See application file for complete search history.

(56) References Cited

U.S. PATENT DOCUMENTS

| | | | |
|---|---|---|---|
| 4,895,727 | A | 1/1990 | Allen |
| 5,445,462 | A | 8/1995 | Johnson et al. |
| 5,590,780 | A | 1/1997 | O'Meara |
| 5,702,694 | A | 12/1997 | Chamness |
| 6,066,124 | A | 5/2000 | Caillouette |
| D436,661 | S | 1/2001 | Berry |
| 6,547,467 | B2 | 4/2003 | Quintero |
| 6,673,031 | B2 | 1/2004 | Mark |
| 6,811,342 | B2 | 11/2004 | Pauchet |
| 8,518,076 | B2 | 8/2013 | Ton |
| 8,871,801 | B2 | 10/2014 | Levitt |
| D771,250 | S | 11/2016 | Zhang et al. |
| D772,407 | S | 11/2016 | Zhang et al. |
| 9,480,691 | B1 | 11/2016 | Roth |
| D801,830 | S | 11/2017 | Zhang et al. |
| 10,195,635 | B2 | 2/2019 | Sporrer |
| D868,160 | S | 11/2019 | Lam |
| 10,745,413 | B2 | 8/2020 | Davidson et al. |
| 2003/0068331 | A1 | 4/2003 | Battaglia et al. |
| 2003/0072814 | A1 | 4/2003 | Maibach et al. |
| 2004/0242770 | A1 | 12/2004 | Feldstein et al. |
| 2004/0254561 | A1 | 12/2004 | Stenton |
| 2005/0019418 | A1 | 1/2005 | Crutchfield et al. |
| 2005/0111900 | A1 | 5/2005 | Fazzolari et al. |
| 2005/0169696 | A1 | 8/2005 | Albisetti |
| 2006/0110415 | A1 | 5/2006 | Gupta |
| 2006/0180613 | A1 | 8/2006 | Manesis |
| 2007/0000566 | A1 | 1/2007 | Gueret |
| 2007/0111954 | A1 | 5/2007 | Crutchfield et al. |
| 2007/0187437 | A1 | 8/2007 | Lord |
| 2008/0146674 | A1 | 6/2008 | Rosenberg et al. |
| 2008/0195040 | A1 | 8/2008 | Clark et al. |
| 2009/0311028 | A1 | 12/2009 | Odermatt et al. |
| 2011/0208136 | A1 | 8/2011 | Sollingen et al. |
| 2011/0212033 | A1 | 9/2011 | Tamarkin et al. |
| 2012/0016320 | A1 | 1/2012 | Lin |
| 2012/0148520 | A1 | 6/2012 | Strobel et al. |
| 2012/0190658 | A1 | 7/2012 | Studin |
| 2012/0312709 | A1 | 12/2012 | Kaufman |
| 2013/0004230 | A1 | 1/2013 | Kirk et al. |
| 2013/0197075 | A1 | 8/2013 | Levitt |
| 2014/0275248 | A1 | 9/2014 | Johnson |
| 2015/0118164 | A1 | 4/2015 | Tamarkin et al. |
| 2016/0193177 | A1 | 7/2016 | Davidson |
| 2017/0305925 | A1* | 10/2017 | Piotrowski ........... C07D 493/08 |
| 2019/0002474 | A1 | 1/2019 | Davidson et al. |
| 2020/0155498 | A1 | 5/2020 | Welgus et al. |
| 2020/0270269 | A1 | 8/2020 | Davidson et al. |

FOREIGN PATENT DOCUMENTS

| | | |
|---|---|---|
| CN | 101108853 A | 1/2008 |
| CN | 101108854 A | 1/2008 |
| CN | 101108853 B | 5/2010 |
| CN | 101798309 A | 8/2010 |
| CN | 101036774 B | 12/2010 |
| CN | 102146086 A * | 8/2011 |
| CN | 102268006 A | 12/2011 |
| CN | 102336765 A | 2/2012 |
| CN | 102526146 A | 7/2012 |
| CN | 202730045 A | 2/2013 |
| CN | 202920809 U | 5/2013 |
| EP | 0841059 A1 | 5/1998 |
| JP | S47-39621 A | 12/1972 |
| JP | 05-058914 A | 3/1993 |
| JP | 10-114626 A | 5/1998 |
| JP | 11-319064 | 11/1999 |
| JP | 11-335303 A | 12/1999 |
| JP | 2005-187330 A | 7/2005 |
| JP | 2007-269693 A | 10/2007 |
| JP | 2010-235471 A | 10/2010 |
| JP | 2013-507367 A | 3/2013 |
| WO | 2012/131238 A1 | 10/2012 |
| WO | WO 2015/027111 A1 | 2/2015 |
| WO | 2016/100732 A2 | 6/2016 |
| WO | WO 2018/226894 A1 | 12/2018 |

OTHER PUBLICATIONS

English Translation of CN 102146086A accessed from Espacenet on Feb. 4, 2020 (Year: 2020).*

Invitation to Pay Additional Fees, dated Aug. 27, 2018, in connection with PCT/US2018/036353.

International Search Report and Written Opinion, dated Oct. 22, 2018, in connection with PCT/US2018/036353.

Supplementary European Search Report, dated Aug. 8, 2018, in connection with EP 16740681.8.

Invitation to Pay Additional Fees, dated Sep. 20, 2018, in connection with PCT/US2018/037808.

International Search Report and Written Opinion, dated Nov. 13, 2018, in connection with PCT/US2018/037808.

Extended European Search Report, dated Oct. 26, 2018, in connection with EP 15871116.8.

Extended European Search Report, dated Dec. 4, 2018, in connection with EP 16740681.8.

Invitation to Pay Additional Fees, dated Dec. 10, 2018, in connection with PCT/US2018/054373.

Aitken et al., Fragmentation patterns in the gas-phase pyrolysis of some bi- and tri-cyclic sulfolanes related to the 8-thiabicyclo[4.3.0]non-3-ene 8,8-dioxide ring system. J Chem Soc. Perkin Transactions 1. 1994;16:2301-2308.

Bouacha et al., A theoretical study of the mechanism, stereoselectivity and Lewis acid catalyst on the Diels-Alder cycloaddition between furan and activated alkenes. Tetrahedron Letters. 2013;54:4030-4033.

Houk et al., On Lewis Acid catalysis of diels-alder reactions. J Am Chem Soc. Jun. 13, 1973;95(12):4094-4096.

Hubbard et al., Lewis Acid Catalyzed Diels-Alder Reactions of Highly Hindered Dienophiles. J. Org. Chem. 1998;63(12):4143-4146.

Hunt et al., Why do catalytic quantities of lewis acid generally yield more product than 1.1 equiv in the intramolecular diels-adler reaction with a furan diene? Competitive complexation NMR studies provide an answer. J Am Chem Soc. 1995;117:1049-1056.

Kharitonov et al., Synthetic transformations of higher terpenoids: VIII. [4+2]-Cycloaddition reactions of lambertianic acid. Russian J Organic Chem. 2003;39(1):57-74.

Lange et al., Synthesis of 4-carboxy-2-thiabicyclo [3.2.0] Heptan-6-ones via 3-carboxy-2,3-dihydrothiophenes: potential β-lactamase inhibitors. Tetrahedron Lett. 1985;26(15): 1791-1794.

Pagni et al., A chemical, spectroscopic, and theoretical assessment of the lewis acidity of LiClO4 in Diethyl Ether. J. Org Chem. 1993;58:3130-3133.

Extended European Search Report, dated Mar. 10, 2017, in connection with EP 14837297.2.

International Search Report and Written Opinion, dated Nov. 20, 2014, in connection with PCT/US2014/052184.

International Search Report and Written Opinion, dated Jul. 14, 2016, in connection with PCT/US2015/066487.

International Preliminary Report on Patentability, dated Jun. 29, 2017, in connection with PCT/US2015/066487.

International Preliminary Report on Patentability, dated Aug. 3, 2017, in connection with PCT/US2016/014139.

(56) References Cited

OTHER PUBLICATIONS

International Search Report and Written Opinion, dated Jul. 1, 2016, in connection with PCT/US2016/014139.
Aono et al., New method for generation of thiocarbonyl ylides from bis(trimethylsilylmethyl) sulfoxides and their application to cycloadditions. Heterocycles. 1995;40(1):249-60.
Bagatell, Studies on Biological Factors in Acantholysis. J Invest Dermatol. Nov. 1964;43:357-61.
Cacchi et al., Palladium-catalyzed carbonylation of enol triflates. A novel method for one-carbon homologation of ketones to α,β-unsaturated carboxylic acid derivatives. Tetrahedron Letters. 26(8), 1985, pp. 1109-1112.
Dang et al., Determination of trace cantharidin in plasma and pharmacokinetic study in beagle dogs using gas chromatography-mass spectrometry. J Anal Toxicol. Sep. 2009;33(7):384-8.
Dauben et al., Organic reactions at high pressure. Cycloadditions with furans. J. Am. Chem. Soc. 1976;98(7): 1992-1993.
Dauben et al., Organic reactions at high pressure. The preparative scale synthesis of cantharidin. J. Org. Chem. 1985;50 (14):2576-2578.
Dauben et al., Simple, efficient total synthesis of cantharidin via a high-pressure Diels-Alder reaction. J. Am. Chem. Soc. 1980;102(22):6893-6894.
Grieco et al., Dramatic rate accelerations of Diels-Alder reactions in 5 M lithium perchlorate-diethyl ether: the cantharidin problem reexamined. J. Am. Chem. Soc. 1990;112(11):4595-4596.
Handy et al., Lithium Trifluoromethanesulfonimide in Acetone or Diethyl-ether as a Safe Alternative To Lithium Perchlorate in Diethyl-ether for Effecting Diels-alder Reactions—nexpected Influence of the Counterion on Exo/endo Selectivity. Synlett 1995;1995(SI):565-567.
Magyarosy et al., Cycloaddition approach to the curing of polyimides via precursor containing thiophene-S,S-dioxide. Hetero Chem. 2006;17(7):648-652.
Mehdinia et al., Analysis of cantharidin in false blister beetles (Coleoptera: Oedemeridae) by headspace solid-phase microextraction and gas chromatography-mass spectrometry. J Chromatogr B Analyt Technol Biomed Life Sci. Oct. 1, 2011;879(27):2897-901. doi:10.1016/j.jchromb.2011.08.020. Epub Aug. 22, 2011.
Nikbakhtzadeh et al., Origin, transfer and distribution of cantharidin-related compounds in the blister beetle Hycleus scabiosae. J Venom Animals Toxins. 2012;18(1):88-96.
Rosenberg et al., Cantharidin treatment of warts at home. Arch Dermatol. Aug. 1977;113(8):1134.
Rudo et al., Cantharidin—als Potenzmittel entzaubert, aber. 2013. Chemie in Unserer Zeit.
Schenck et al., Ausfuhrliche Mitteilung erfolgt an anderer Stelle. Naturwissenshaften Oct. 15, 1953; 40: 581.
Stork et al., A Stereospecific Synthesis of Cantharidin. J. Am. Chem. Soc., 1953;75(2):384-392.
Stork et al., Cantharidin. A Stereospecific Total Synthesis. J. Am. Chem. Soc. 1951;73(9):4501-4501.
Terao et al., Thiocarbonyl Ylides. VI. New Generation of Thiocarbonyl Ylides from Organosilicon Compounds Containing Sulfur and Their 1, 3-Cycloadditions. J-STAGE. 1987;35(5):1734-1740.
White et al., Dihydrothiophenes as precursors to fused quinolines, quinolones and coumarins via o-quinodimethane intermediates. Tetrahedron 52(9), Feb. 26, 1996, pp. 3117-3134.
International Search Report and Written Opinion, dated Apr. 3, 2019 in connection with PCT/US2018/054373.

Anderson et al., Practical Process Research and Development. 1st Edition. Academic Press. Mar. 20, 2000 81-111.
Augé et al., Catalysis by Lithium Cation: Lithium Trifluoromethanesulfonate as a Substitute for Lithium Perchlorate in Cycloadditions. Synlett 2000;6:877-9.
Hollis et al., Homogeneous catalysis. Titanium complex [Ti(Cp)$_2$(CF$_3$SO$_3$)$_2$] and zirconium complex [Zr(Cp)$_2$(CF$_3$SO$_3$)$_2$THF], efficient catalysts for the Diels-Alder reaction. Organometallics. Aug. 1, 1992;11(8):2745-8. https://doi.org/10.1021/om00044a004.
Prabhakar Reddy et al., Synthesis, cytotoxic activity and structure-activity relationships of hedychenone analogues. Bioorg Med Chem Lett. Apr. 15, 2010;20(8):2525-8. doi: 10.1016/j.bmcl.2010.02.101. Epub Mar. 3, 2010.
Song et al., Ionic liquids as powerful media in scandium triflate catalysed Diels-Alder reactions: significant rate acceleration, selectivity improvement and easy recycling of catalyst. Chem Commun. 2001;12:1122-3.
U.S. Appl. No. 16/619,675, filed Dec. 5, 2019, Welgus et al.
U.S. Appl. No. 16/621,854, filed Dec. 12, 2019, Davidson et al.
U.S. Appl. No. 16/753,660, filed Apr. 3, 2020, Davidson et al.
PCT/US2018/037808, dated Dec. 26, 2019, International Preliminary Report on Patentability.
PCT/US2018/054373, dated Apr. 16, 2020, International Preliminary Report on Patentability.
International Preliminary Report on Patentability dated Dec. 26, 2019 in connection with International Application No. PCT/US2018/037808.
International Preliminary Report on Patentability dated Apr. 16, 2020, in connection with International Application No. PCT/US2018/054373.
[No. Author Listed] CAS RN 27607-77-8. Entered STN: Nov. 16, 1984. 28 pages.
[No. Author Listed] CAS RN 76262-87-8. Entered STN: Nov. 16, 1984. 19 pages.
[No. Author Listed] CAS RN 89672-77-5. Entered STN: Nov. 16, 1984. 29 pages.
Braddock et al., Stereochemistry of the Catalysed Diels-Alder Reaction between Cyclopentadiene and Dimethyl Monothionofumarate; Soft versus Hard Lewis Acids. J. Chem. Soc. Chem. Commun. Jan. 1, 1993;16:1244-6. doi: https://doi.org/10.1039/C39930001244.
Hollis et al., Homogenous Catalysis: Transition Metal Based Lewis Acid Catalysts. Tetrahedron. 1993;49(25):5415-30. doi: https://doi.org/10.1016/S0040-4020(01)87259-8.
Huang, Catalysts for Hetero Diels-Alder Reaction of Imines. Chinese Journal of Organic Chemistry. Oct. 2003;23(10): 1064-75.
Sperry et al., Studies on the Diels-Alder reaction of annulated furans: application to the synthesis of substituted phenanthrenes. Tetrahedron Letters. Apr. 18, 2005;46(16):2789-93. Doi: 10.1016/j.tetlet.2005.02.148.
Tseng et al., Synthesis and Evaluation of Cantharidinimides on Human Cancer Cells. J Exp Clin Med. Oct. 2012;4(5):280-283.
Verma et al., Bioactive component, cantharidin from Mylabris cichorii and its antitumor activity against Ehrlich ascites carcinoma. Cell Biol Toxicol. Jun. 2012;28(3):133-47. doi: 10.1007/S10565-011-9206-6. Epub Mar. 9, 2012.
Kronemyer et al., Verrica develops a solution for common warts. Retrieved from www.dermatologytimes.com. Nov. 13, 2017. 1 page.

\* cited by examiner

HPLC METHOD

- Column: Kinetex C18 2.6μm, 10 x 0.46cm – Phenomenex
- UV Wavelength (nm): 205
- Flow rate (mL/min): 1.0
- Oven Temp. (°C): 30
- Injection volume (μL): 10
- Analysis time (min): 28 (record from 0 to 17 min)

Gradient:

| Time (min) | A (%) | B (%) |
|---|---|---|
| 0 | 85 | 15 |
| 12 | 10 | 90 |
| 17 | 10 | 90 |
| 18 | 85 | 15 |
| 28 | 85 | 15 |

Mobile Phase
Phase A: H2O pH 3 (H3PO4)
Phase B: ACN

Dissolution solvent: ACN

Nominal concentration (mg/ml): 8

FIG. 2

QUANTIFICATION AND PREPARATION OF PHARMACEUTICAL GRADE CANTHARIDIN

CROSS-REFERENCE TO RELATED APPLICATIONS

The present application is a national stage filing under 35 U.S.C. § 371 of international PCT application, PCT/US2016/014139, filed Jan. 20, 2016, which claims priority under 35 U.S.C. § 119(e) to U.S. Provisional Patent Application U.S. Ser. No. 62/105,622, filed Jan. 20, 2015, each of which is incorporated herein by reference.

BACKGROUND

Warts are small epidermal skin growths caused by viral infections, often found on the hands or feet. The most common type of wart is called *Verruca vulgaris*, which can be caused by multiple different strains of the Human papilloma virus (HPV). On most parts of the body these warts may be referred to as common warts; on feet, however, they may be referred to as plantar warts when on the feet or genital warts or condoloma when on the genitals. Other epidermal viral conditions, such as Molluscum contagiosum, may resemble warts but may be caused by distinct viruses. These viral mediated skin growths may be unsightly and may have a significant risk for cancerous transformation and for spreading, making their removal desirable. Other superficial hyper-proliferative disorders may resemble warts but may be caused by non-viral mechanisms, and may include seborrheic keratosis, actinic keratosis and porokeratosis.

Multiple approaches have been used to remove warts and related diseases, including cryotherapy; surgical curettage; laser treatment; irritants such as salicylic acid and zinc oxide; acids such as nitric acid and squaric acid, immunotherapeutics such as imiquimod, 2,4-Dinitrochlorobenzene and *Candida* antigen, and chemotherapeutics, such as bleomyocin, podophyllotoxin and 5-fluorouracil. Some of these therapies may be painful, while others may leave disfiguring scars and/or require daily application. Some of these cutaneous disorders may remain recalcitrant even after multiple follow-up treatments.

Cantharidin (1,2-Dimethyl-3,6-epoxyperhydrophthalic anhydride) is a lipophilic compound that may be used in the treatment of various medical conditions, including the cutaneous disorders described above. Cantharidin is an odorless colorless crystalline solid at room temperature. Some methods of purifying cantharidin may leave impurities behind to provide preparations that may not be suitable for therapeutic use.

SUMMARY

Recognized herein are methods to detect impurities, purify cantharidin and generate cantharidin preparations (or formulations). The present disclosure provides cantharidin preparations that may have improved properties for treatment of various ailments, such as skin conditions (e.g., warts). Preparations of the present disclosure may be have improved therapeutic properties relative to other approaches for treating such skin conditions.

In an aspect, the present disclosure provides for method for processing a cantharidin preparation, comprising: (a) loading the cantharidin preparation comprising cantharidin over a stationary phase under conditions that are sufficient to immobilize the cantharidin onto the stationary phase; and (b) washing the stationary phase with one or more mobile phases under washing conditions that are sufficient to yield an elution stream from the stationary phase, which elution stream exhibits one or more peaks from about 200 nanometers (nm) to 210 nm under ultraviolet (UV) absorbance spectroscopy. In some embodiments, the elution stream exhibits one or more peaks at about 205 nanometers (nm) under UV absorbance spectroscopy. In some embodiments, the elution stream exhibits a plurality peaks at about 205 nanometers (nm) under UV absorbance spectroscopy. The washing may be continuous or discontinuous.

In some embodiments, the method further comprises monitoring eluents from the stationary phase at an absorbance wavelength less than 228 nm while washing the stationary phase. In some embodiments, the method further comprises monitoring eluents from the stationary phase at an absorbance wavelength less than 220, 215, 210, or 209 nm while washing the stationary phase. In some embodiments, the elution stream exhibits at least three peaks at about 205 nm under UV absorbance spectroscopy. In some embodiments, the elution stream exhibits at least five peaks at about 205 nm under UV absorbance spectroscopy. In some embodiments, the plurality of peaks is detectable at a limit of quantification of 0.05% of the total peak area at the target wavelength. In some embodiments, the plurality of peaks are detectable at a limit of detection of less than 0.02% of the total peak area at the target wavelength. In some embodiments, a given mobile phase of the one or more mobile phases comprises water with a pH from about 3 to about 7 buffered with an acid. In some embodiments, the acid is selected from the group consisting of: phosphoric acid, sulfuric acid, hydrochloric acid, acetic acid, trifloric acid, and any combination thereof. In some embodiments, a given mobile phase of the one or more mobile phases comprises about 100% of an organic solvent selected from the group consisting of: DMSO, acetone, chloroform, diethyl ether, ethanol, acetonitrile, methanol, and any combination thereof. In some embodiments, the washing is performed with a gradient of the one or more mobile phases. In some embodiments, the gradient starts with 85% of a first mobile phase of the one or more mobile phases, and 15% of a second mobile phase of the one or more mobile phases and proceeds at 10% of the first mobile phase and 90% of the second mobile phase upon the loading. In some embodiments, the stationary phase is part of an apparatus selected from an HPLC purification apparatus, an LC-MS purification apparatus, and a GC-MS purification apparatus, or any combination thereof. In some embodiments, the stationary phase comprises a C18 column. In some embodiments, the washing is performed at about 1 mL/minute. In some embodiments, the elution stream comprises cantharidin-associated impurities. In some embodiments, the elution stream comprises cantharidin. In some embodiments, the cantharidin preparation comprises a recrystallized cantharidin preparation. In some embodiments, the recrystallized cantharidin comprises at least 98.7% cantharidin. In some embodiments, the recrystallized cantharidin preparation comprises a total concentration of impurities below 1.3%. In some embodiments, the recrystallized cantharidin preparation has a reduced concentration of a cantharidin-associated impurity compared to a non-recrystallized cantharidin preparation. In some embodiments, the recrystallized cantharidin has a concentration of a cantharidin-associated impurity that is reduced by at least 80%. In some embodiments, the recrystallized cantharidin preparation comprises one or more cantharidin-associated impurities at a concentration below 0.15%. In some embodiments, the recrystallized cantharidin preparation comprises one or more cantharidin-associated impurities at a concentration below 0.1%. In some embodiments, the recrystallized cantharidin preparation comprises one or more cantharidin-associated impurities at a concentration below 0.05% or less. In some embodiments, the recrystallized cantharidin preparation comprises cantharidin-associated impurities at levels below International Conference of Harmonization (ICH) detection limits. In some embodiments, the cantharidin-associated impurities comprise an impurity with a relative retention time (RRT) selected from the group consisting of: RRT 0.53, RRT 0.63, RRT 0.71, RRT 0.72, RRT 0.75, RRT 1.19, RRT 1.26, RRT 1.30, RRT 1.42, RRT 1.71, RRT 1.92, RRT 2.6, and RRT 2.85, or any combination thereof. In some embodiments, the cantharidin-associated impurities comprise an impurity with an RRT from 0.25 to 5. In some embodiments, the cantharidin preparation comprises a cantharidin extract derived from a beetle. In some embodiments, the cantharidin preparation comprises a synthetic cantharidin. In some embodiments, the cantharidin preparation comprises one or more cantharidin derivatives. In some embodiments, the washing is continuous.

In another aspect, the present disclosure provides a method for preparing a formulated drug product containing cantharidin or a cantharidin extract so that it may be analyzed for purity or stability with the above methods.

In another aspect, the present disclosure provides a method for analyzing a drug product containing or suspected of containing cantharidin, comprising: (a) adding a diluent to a drug product containing or suspected of containing cantharidin and at least one excipient to form a mixture, wherein the at least one excipient interferes with liquid chromatography analysis of cantharidin, cantharidin derivatives, or cantharidin associated excipients; (b) from the mixture, generating a solution having a reduced amount or concentration of the at least one excipient compared to the mixture; and (c) analyzing at least a portion of the solution using liquid chromatography.

In some embodiments, (b) comprises centrifuging the mixture under conditions that are sufficient to produce the solution from the mixture that comprises a reduced amount or concentration of the at least one excipient compared to the mixture. In some embodiments, the liquid chromatography comprises high performance liquid chromatography (HPLC).

In another aspect, the present disclosure provides a method for purifying cantharidin, comprising: (a) providing a first cantharidin preparation comprising cantharidin and a cantharidin-associated impurity, wherein the first cantharidin preparation has a first cantharidin concentration; (b) subjecting the first cantharidin preparation to sublimation conditions that are sufficient to produce a sublimation stream comprising at least a portion of the cantharidin and at least a portion of the cantharidin-associated impurity, wherein under the sublimation conditions the cantharidin-associated impurity sublimates at a reduced rate compared to the cantharidin; and (c) forming from the sublimation stream a second preparation of cantharidin preparation comprising cantharidin at a second cantharidin concentration that is greater than the first cantharidin concentration.

In some embodiments, the second cantharidin preparation comprises at least 70% fewer cantharidin-associated impurities than the first cantharidin preparation. In some embodiments, the first cantharidin preparation comprises one or more cantharidin derivatives. In some embodiments, the second cantharidin preparation has a peak melting point of greater than 216.07° C. In some embodiments, the second cantharidin preparation has a narrower melting point range than the first cantharidin preparation. In some embodiments, the second cantharidin preparation has a higher peak melting point than the first cantharidin preparation. In some embodiments, the sublimation conditions comprise heating the first cantharidin preparation to a temperature from about 82° C. to about 210° C. In some embodiments, the second cantharidin preparation has a greater solubility than the first cantharidin preparation. In some embodiments, the second cantharidin preparation has a greater stability than the first cantharidin preparation. In some embodiments, the second cantharidin preparation has a longer shelf life than the first cantharidin preparation. In some embodiments, the second cantharidin preparation has a more uniform crystal size distribution than the first cantharidin preparation. In some embodiments, the second cantharidin preparation has a reduced water content compared to the first cantharidin preparation. In some embodiments, the second cantharidin preparation has a reduced toxicity compared to the first cantharidin preparation. In some embodiments, the second cantharidin preparation has a reduced total plate count compared to the first cantharidin preparation. In some embodiments, the second cantharidin preparation has a reduced yeast and mold count compared to the first cantharidin preparation. In some embodiments, the second cantharidin preparation has a reduced loss on drying compared to the first cantharidin preparation. In some embodiments, the second cantharidin preparation has a reduced residue on ignition compared to the first cantharidin preparation. In some embodiments, the second cantharidin preparation has a reduced proportion of crystals smaller than 100 μm compared to the first cantharidin preparation. In some embodiments, the second cantharidin preparation comprises a distinct crystal polymorph from the first cantharidin preparation.

In another aspect, the present disclosure provides a method for purifying cantharidin, comprising: (a) providing a first cantharidin preparation comprising cantharidin and a cantharidin-associated impurity, wherein the first cantharidin preparation has a first cantharidin concentration; (b) heating the first cantharidin preparation and dissolving the first cantharidin preparation into a solvent to generate a solution comprising the cantharidin and the cantharidin-associated impurity; and (c) cooling the solution, thereby precipitating from the solution a second cantharidin preparation, wherein, during the cooling, the cantharidin precipitates at a higher rate as compared to the cantharidin-associated impurity.

In some embodiments, the second cantharidin preparation comprises at least 70% lower concentration of the cantharidin-associated impurity than the first cantharidin preparation. In some embodiments, the heating comprises heating the first cantharidin preparation to a temperature from about 50° C. to about 80° C. In some embodiments, the heating comprises heating the first cantharidin preparation to a temperature of about 70° C. to about 80° C. In some embodiments, the cooling comprises cooling the solution to a temperature from about 0° C. to about 30° C. In some embodiments, the cooling comprises cooling the solution to a temperature of about 5° C. to about 15° C. In some embodiments, the method further comprises drying the second cantharidin preparation. In some embodiments, the second cantharidin preparation exhibits a plurality of peaks at about 205 nanometers (nm) when subjected to ultraviolet (UV) absorbance spectroscopy. In some embodiments, the second cantharidin preparation has a peak melting point of greater than 216.07° C. In some embodiments, the second cantharidin preparation has a narrower melting point range than the first cantharidin preparation. In some embodiments, the second cantharidin preparation has a higher peak melting point than the first cantharidin preparation. In some embodiments, the second cantharidin preparation has higher solubility than the first cantharidin preparation. In some embodiments, the second cantharidin preparation has improved stability compared to the first cantharidin preparation. In some embodiments, the second cantharidin preparation has a longer shelf life than the first cantharidin preparation. In some embodiments, the second cantharidin preparation has a more uniform crystal size distribution than the first cantharidin preparation. In some embodiments, the second cantharidin preparation has a reduced water content compared to the first cantharidin preparation. In some embodiments, the second cantharidin preparation has a reduced toxicity compared to the first cantharidin preparation. In some embodiments, the second cantharidin preparation has a reduced total plate count compared to the first cantharidin preparation. In some embodiments, the second cantharidin preparation has a reduced yeast and mold count compared to the first cantharidin preparation. In some embodiments, the second cantharidin preparation has a reduced loss on drying compared to the first cantharidin preparation. In some embodiments, the second cantharidin preparation has a reduced residue on ignition compared to the first cantharidin preparation. In some embodiments, the second cantharidin preparation has a reduced proportion of crystals with particle sizes less than 100 μm as compared to the first cantharidin preparation. In some embodiments, the second cantharidin preparation has a reduced proportion of crystals with particle sizes less than 10 μm as compared to the first cantharidin preparation. In some embodiments, the second cantharidin preparation comprises a distinct crystal polymorph from the first cantharidin preparation.

In another aspect, the present disclosure provides a cantharidin preparation comprising cantharidin, wherein the cantharidin preparation is characterized by a melting point greater than 216.07° C.

In another aspect, the present disclosure provides a cantharidin preparation comprising cantharidin and less than 2.1% water.

In another aspect, the present disclosure provides a cantharidin preparation comprising cantharidin, wherein the cantharidin preparation is characterized by a residue on ignition of less than 3%.

In another aspect, the present disclosure provides a cantharidin preparation comprising cantharidin and less than 19 parts per million (ppm) of heavy metals and/or less than 1.9 ppm arsenic.

In some embodiments, the cantharidin preparation comprises less than 19 ppm of heavy metals and less than 1.9 ppm of arsenic.

In another aspect, the present disclosure provides a cantharidin preparation comprising cantharidin and at least any one of (i) less than 250 parts per million (ppm) hexane, (ii) less than 3800 ppm cyclohexane, and (iii) less than 4900 ppm acetone and ethanol.

In some embodiments, the cantharidin preparation comprises at least any two of (i) less than 250 ppm hexane, (ii) less than 3800 ppm cyclohexane, and (iii) less than 4900 ppm acetone and ethanol. In some embodiments, the cantharidin preparation comprises (i) less than 250 ppm hexane, (ii) less than 3800 ppm cyclohexane, and (iii) less than 4900 ppm acetone and ethanol.

In another aspect, the present disclosure provides a cantharidin preparation comprising cantharidin, wherein the cantharidin preparation is characterized by a total plate count of less than 125 colony forming units per gram (cfu/g).

In another aspect, the present disclosure provides a cantharidin preparation comprising cantharidin, wherein the cantharidin preparation is characterized by a yeast and mold count of less than 50 colony forming units per gram (cfu/g).

In another aspect, the present disclosure provides a cantharidin preparation comprising cantharidin, wherein the cantharidin preparation is characterized by a crystal polymorph under X-ray Powder Diffraction that is different than that shown in FIG. 10.

In another aspect, the present disclosure provides a cantharidin preparation comprising cantharidin, wherein the cantharidin preparation is characterized by a crystal size polydispersity index less than about 10.

In some embodiments, the cantharidin preparation further comprises an excipient.

In some embodiments, the cantharidin preparation further comprises a flavorant and/or a colorant.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." and "FIGS." herein), of which:

FIG. 2 illustrates an exemplary cantharidin purification method of the disclosure;

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Cantharidin

The term "cantharidin-associated impurity," as used herein, generally refers to any natural or synthetic molecule or substance that is not cantharidin which elutes from an HPLC column with a relative retention time (RRT) from about 0.25 to about 5 compared to cantharidin. A cantharidin-associated impurity may be in the cantharidin extract loaded onto an HPLC column. A cantharidin-associated impurity may form during the HPLC run. Cantharidin-associated impurities can reduce the melting point of a cantharidin preparation. Cantharidin-associated impurities may be toxic. Cantharidin-associated impurities may reduce the efficacy of a cantharidin preparation. Cantharidin-associated impurities may breakdown into or react with other compounds reducing the overall stability of a cantharidin preparation. Cantharidin-associated impurities may be poorly soluble or reduce the overall solubility of a cantharidin preparation.

Figure 1:
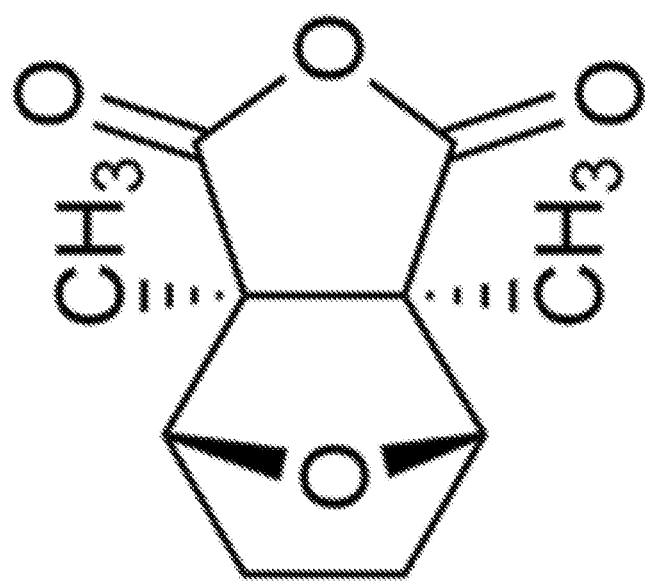
FIG. 1 depicts the chemical structure of cantharidin.

The term "cantharidin," as used herein, generally refers to 1,2-Dimethyl-3,6-epoxyperhydrophthalic anhydride, a lipophilic compound that is a furan molecule. Cantharidin can be obtained from the body fluids of the blister beetle, primarily of the family Meloidae. Cantharidin can be used for the treatment of various skin conditions including but not limited to common warts and Molluscum contagiosum. Cantharidin is an odorless colorless crystalline solid at room temperature. As used herein, "cantharidin" may be used interchangeably with cantharidin, cantharone, and kantaridin. The structure of cantharidin is shown in FIG. 1. Table 1 lists some exemplary features of cantharidin.

Figure 6:
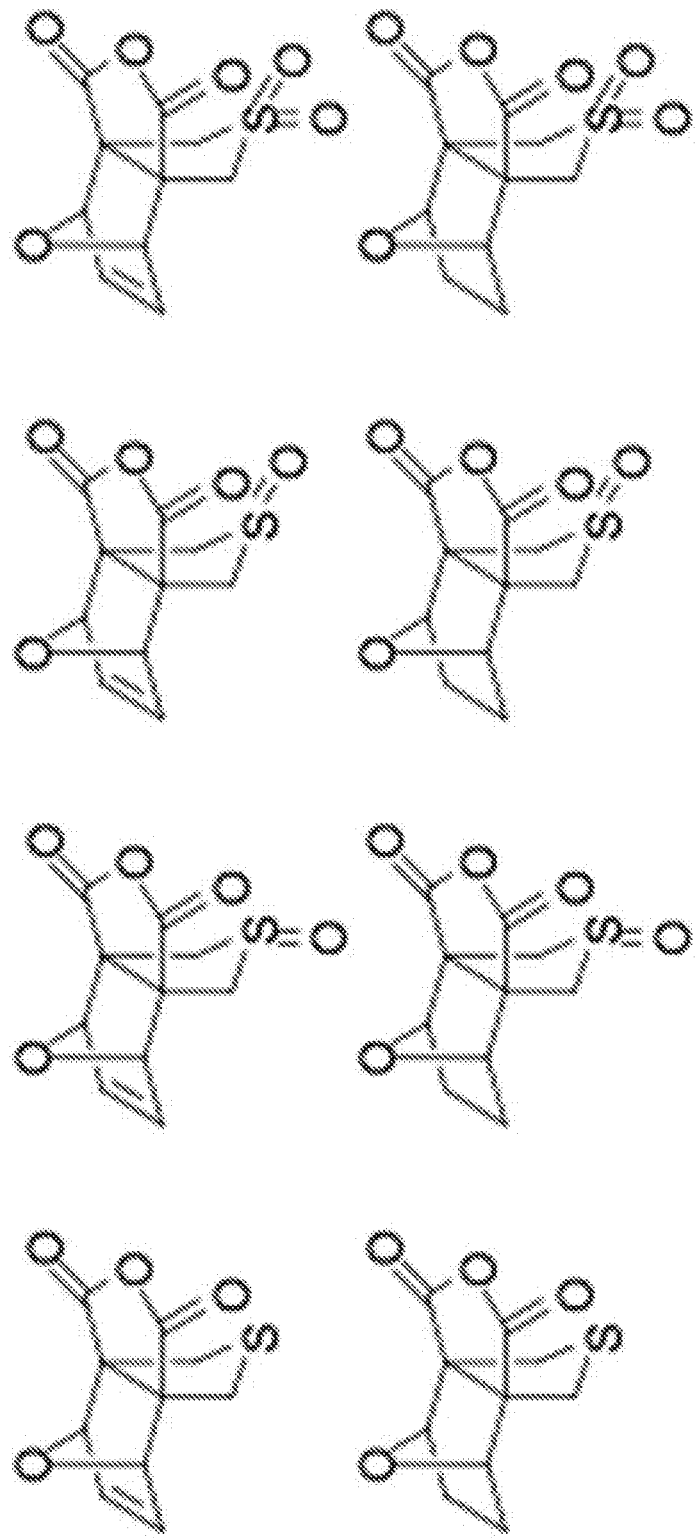
FIG. 6 depicts examples of cantharidin derivatives that may be used in the purification and detection methods of the disclosure.

The term "cantharidin derivative" as used in herein, generally refers to any compound that is similar to cantharidin (e.g., having a sulfur or sulfoxide group bound). A cantharidin derivative can be synthetic. A cantharidin derivative can have similar biological (e.g., therapeutic) activity as cantharidin. Examples of cantharidin derivatives are shown in FIG. 6.

The term "preparation of cantharidin" or "cantharidin preparation" as used herein, generally refers to a synthetic or natural extract comprising one or more of cantharidin, a cantharidin-associated impurity, a cantharidin derivative, or any combination thereof.

The term "drug product" as used herein, generally refers to a formulation containing cantharidin or a cantharidin derivative and at least one excipient prepared for the treatment, cure or prevention of a disease or medical condition.

TABLE 1

Features of cantharidin.

| Formula | $C_{10}H_{12}O_4$ |
| --- | --- |
| Molecular Weight | 196.20 g/mol |
| Melting Point | 212-218° C. |
| CAS Reg No. | 56-25-7 |

Cantharidin may not readily absorb in the ultra violet (UV) spectrum, having no strong chromophore, and may not be detectable with standard high-performance liquid chromatography (HPLC) methods or with alternative methods such as liquid chromatography mass spectrometry (LC-MS).

The methods described herein can provide for reliable and accurate determination of the overall purity and impurity profile of cantharidin preparations with high sensitivity. The methods provide for high-yielding methods for purifying crude cantharidin extracts or synthetic cantharidin material into ultra-pure cantharidin. The extracts prepared by the methods of the disclosure may be suitable for use in pharmaceutical products.

Crude preparations of cantharidin can be known as cantharides or mylabris or mylabris extract. An extract of cantharidin prepared with the methods of the disclosure can be at least about 70, 75, 80, 85, 90, 95, 96, 97, 98, 99, 99.1, 99.15, 99.2, 99.25, 99.3, 99.35, 99.4, 99.45, 99.5, 99.95, 99.6, 99.65, 99.7, 99.75, 99.8, 99.85, 99.9, 99.95, or 99.99%, or even 100% pure (i.e., free of impurities). An extract of cantharidin prepared with the methods of the disclosure can be at most about 70, 75, 80, 85, 90, 95, 96, 97, 98, 99, 99.1, 99.15, 99.2, 99.25, 99.3, 99.35, 99.4, 99.45, 99.5, 99.95, 99.6, 99.65, 99.7, 99.75, 99.8, 99.85, 99.9, 99.95, 99.99, or 100% pure (i.e., free of impurities).

The percentage of total impurities can be less than about 10.00%%, 5.00%, 4.00%, 3.00%, 2.00%, 1.00%, 0.5%, 0.3%, 0.29%, 0.28%, 0.27%, 0.26%, 0.25%, 0.24%, 0.23%, 0.22%, 0.21%, 0.20%, 0.19%, 0.18%, 0.17%, 0.16%, 0.15%, 0.14%, 0.13%, 0.12%, 0.11%, 0.10%, 0.09%, 0.08%, 0.07%, 0.06%, 0.05%, 0.03%, 0.02%, 0.01%, 0.009%, 0.008%, 0.007%, 0.006%, 0.005%, 0.004%, 0.003%, 0.002%, or 0.001%, or less. The percentage of total impurities can be greater than about 10.00%, 5.00%, 4.00%, 3.00%, 2.00%, 1.00%, 0.5%, 0.3%, 0.29%, 0.28%, 0.27%, 0.26%, 0.25%, 0.24%, 0.23%, 0.22%, 0.21%, 0.20%, 0.19%, 0.18%, 0.17%, 0.16%, 0.15%, 0.14%, 0.13%, 0.12%, 0.11%, 0.10%, 0.09%, 0.08%, 0.07%, 0.06%, 0.05%, 0.03%, 0.02%, 0.01%, 0.009%, 0.008%, 0.007%, 0.006%, 0.005%, 0.004%, 0.003%, 0.002%, or 0.001%.

Exemplary cantharidin-related impurities can include RRT (relative retention time) 2.85, RRT 0.63, impurities present in insects (e.g., blister beetles), and synthetic impurities (e.g., not naturally occurring in blister beetles or the cantharidin extract).

The method can reduce impurities below ICH (International Conference of Harmonization) Quantification limits. The method can reduce impurities below the ICH toxicology limit of 0.15% or less. The method can reduce impurities below the ICH quantification limit of at least 0.3%, 0.25%, 0.2%, 0.15%, 0.1%, 0.05%, or 0.01% or less. The method can reduce impurities below the ICH quantification limit of at most 0.3%, 0.25%, 0.2%, 0.15%, 0.1%, 0.05%, or 0.01% or less. The method can reduce impurities below ICH detection limits of at least 0.25%, 0.2%, 0.15%, 0.1%, 0.05%, 0.01%, 0.005%, or 0.001% or less. The method can reduce impurities below 0.05%, 0.01%, 0.005%, or 0.001% or less. Specific impurities such as RT 2.85 can be reduced below the ICH detection limit. The method can reduce impurities below the ICH quantification limit of 0.10% or less. The method can reduce impurities below ICH detection limits of 0.05% or less.

Methods of the present disclosure can bring the purity of the material to at least about 50%, 60%, 70%, 80%, 90%, 95%, 98%, 98.5%, 99.0%, 99.1%, 99.2%, 99.3%, 99.4%, 99.5%, 99.6%, 99.7%, 99.8%, or 99.9%, or even 100%, for example with a limit of quantification greater than 0.05% at wavelengths between 180-300 (e.g., 205, 228, 273 nanometers or more).

Methods of the present disclosure can bring the peak melting point of the material to at least about 212, 213, 214, 215, 216, 217, 217.1, 217.2, 217.3, 217.4, 217.5, 217.6, 217.7, 217.8, 217.9 or 218.0° C. In some cases, methods of the present disclosure can bring the peak melting point of the material to at most about 212, 213, 214, 215, 216, 217, 217.1, 217.2, 217.3, 217.4, 217.5, 217.6, 217.7, 217.8, 217.9 or 218.0° C.

Methods of the present disclosure can improve the stability of the material so that it, or products formulated from it, have a greater stability and thus a longer shelf life. For example, methods of the present disclosure can result in compositions with a stability or shelf life at least 10%, 20%, 30%, 40%, 50%, 60%, 70%, 80%, 90%, 100%, 200%, 300%, 400%, 500%, 600%, 700%, 800%, 900%, 1000%, or more compared to a composition prior to use of methods of the present disclosure. Methods of the present disclosure can result in compositions with a shelf life (e.g., when stored in a cool, dry place away from strong light and heat) of greater than 3, 3.5, 4, 4.5, 5, 5.5, 6, 6.5, 7, 7.5, 8, 8.5, 9, 9.5, or 10 years.

Methods of the present disclosure can change the size or form of the crystal habit and can improve or reduce variability in the solubility of the material in a solvent or drug product formulation. For example, methods of the present disclosure can result in compositions with a variability in solubility at least 10%, 20%, 30%, 40%, 50%, 60%, 70%, 80%, 90%, 95%, 96%, 97%, 98%, 99%, 99.9%, 99.99%, or 99.999% less than a composition prior to use of methods of the present disclosure.

Methods of the present disclosure can decrease the toxicity (e.g., toxicity to a subject, such as a human) of the material by removing impurities, increasing the average crystal size, or by eliminating fine particulate material that may be inhaled or easily dispersed. For example, average crystal size can be increased by at least 10%, 20%, 30%, 40%, 50%, 60%, 70%, 80%, 90%, 100%, 200%, 300%, 400%, 500%, 600%, 700%, 800%, 900%, 1000%, or more compared to a composition prior to use of methods of the present disclosure. Toxicity can be reduced by at least 10%, 20%, 30%, 40%, 50%, 60%, 70%, 80%, 90%, 95%, 96%, 97%, 98%, 99%, 99.9%, 99.99%, or 99.999% compared to a composition prior to use of methods of the present disclosure.

Methods of the present disclosure can decrease the polydispersity of the crystal sizes in a cantharidin preparation. For example, crystal size polydispersity can be reduced by at least about 10%, 20%, 30%, 40%, 50%, 60%, 70%, 80%, 90%, or 100%. In some instances, the crystal size polydispersity is reduced by at most about 10%, 20%, 30%, 40%, 50%, 60%, 70%, 80%, 90%, or 100%. The polydispersity index of a cantharidin preparation prepared by techniques disclosed herein can be less than or equal to about 100, 90, 80, 70, 60, 50, 40, 30, 20, 10, 9, 8, 7, 6, 5, 4.5, 4.0, 3.5, 3.0, 2.5, 2.0, 1.9, 1.8, 1.7, 1.6, 1.5, 1.4, 1.3, 1.2, 1.1, 1.09, 1.08, 1.07, 1.06, 1.05, 1.04, 1.03, 1.02, 1.01, or 1.

Figure 10:
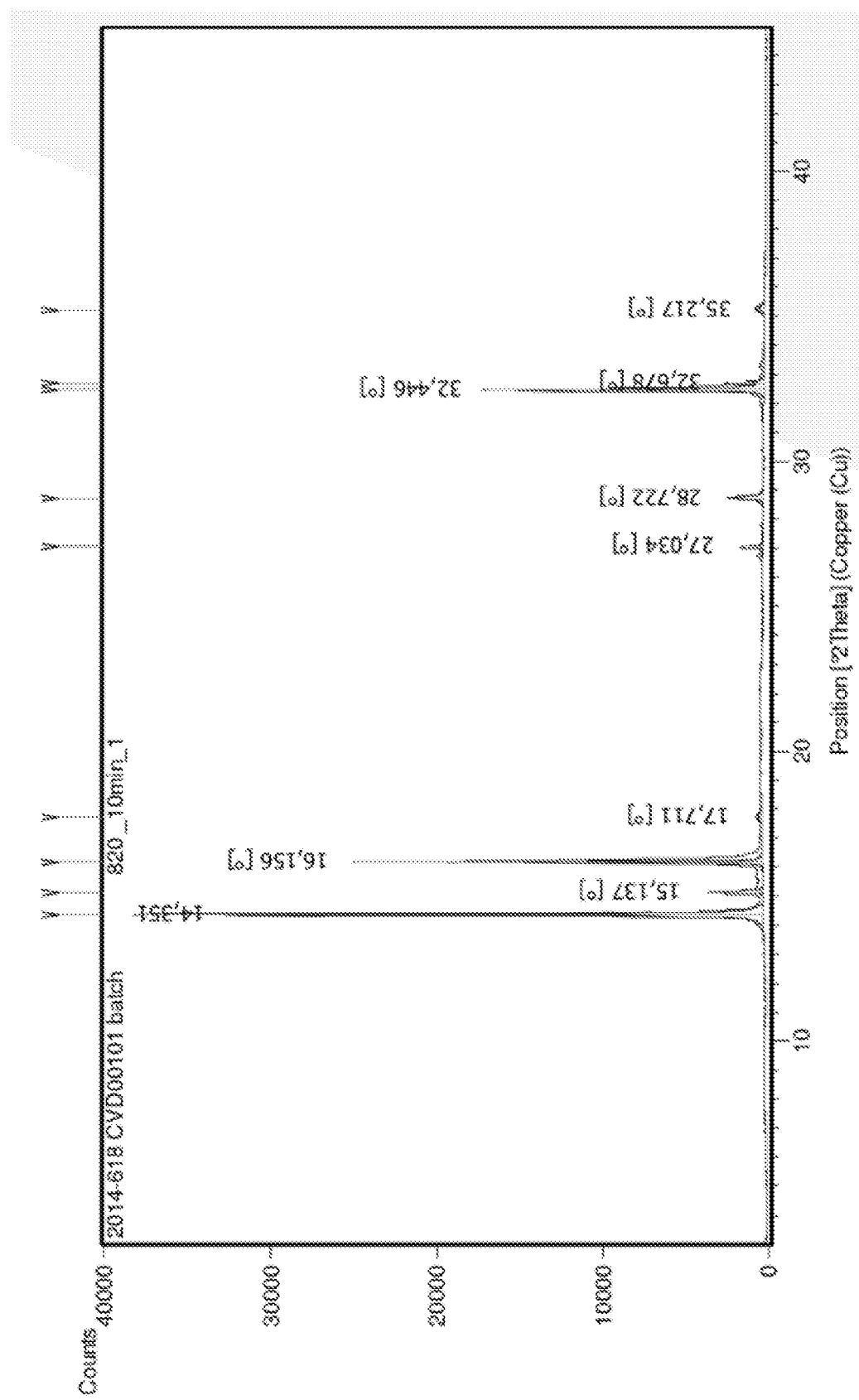
FIG. 10 shows an X-ray Powder Diffraction (XRPD) analysis pattern of a crude cantharidin preparation.

Methods of the present disclosure can result in a different crystal structure polymorphism than the starting material. For example, FIG. 10 shows an exemplary X-ray Powder Diffraction (XRPD) analysis pattern of a crude cantharidin preparation. In some cases, techniques of the present disclosure can result in a cantharidin preparation of a different polymorph than that shown in FIG. 10.

The method can reduce the microbial load of the starting material. The microbial load can be reduced by at least about 10%, 20%, 30%, 40%, 50%, 60%, 70%, 80%, 90%, or 100%. In some instances, the microbial load is reduced by at most about 10%, 20%, 30%, 40%, 50%, 60%, 70%, 80%, 90%, or 100%.

The method can reduce endotoxin levels. Endotoxin levels can be reduced by at least about 10%, 20%, 30%, 40%, 50%, 60%, 70%, 80%, 90%, or 100%. In some instances, endotoxin levels are reduced by at most about 10%, 20%, 30%, 40%, 50%, 60%, 70%, 80%, 90%, or 100%.

The method can reduce pesticide, fungicide, herbicide or insecticide levels. Pesticide, fungicide, herbicide or insecticide levels can be reduced by at least 10%, 20%, 30%, 40%, 50%, 60%, 70%, 80%, 90%, or 100%. In some instances, pesticide, fungicide, herbicide or insecticide levels are reduced by at most about 10%, 20%, 30%, 40%, 50%, 60%, 70%, 80%, 90%, or 100%.

The method can reduce heavy metal levels. Heavy metal levels can be reduced by at least 10%, 20%, 30%, 40%, 50%, 60%, 70%, 80%, 90%, or 100%. In some instances, heavy metal levels are reduced by at most about 10%, 20%, 30%, 40%, 50%, 60%, 70%, 80%, 90%, or 100%. Heavy metal levels can be less than about 20 parts per million (ppm), 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, or 1 ppm.

The method can reduce arsenic levels. Arsenic levels can be reduced by at least 10%, 20%, 30%, 40%, 50%, 60%, 70%, 80%, 90%, or 100%. In some instances, arsenic levels are reduced by at most about 10%, 20%, 30%, 40%, 50%, 60%, 70%, 80%, 90%, or 100%. Arsenic levels can be less than about 2 ppm, 1.9 ppm, 1.8 ppm, 1.7 ppm, 1.6 ppm, 1.5 ppm, 1.4 ppm, 1.3 ppm, 1.2 ppm, 1.1 ppm, 1 ppm, 0.9 ppm, 0.8 ppm, 0.7 ppm, 0.6 ppm, 0.5 ppm, 0.4 ppm, 0.3 ppm, 0.2 ppm, or 0.1 ppm.

The method can reduce solvent. Solvent levels can be reduced by at least 10%, 20%, 30%, 40%, 50%, 60%, 70%, 80%, 90%, or 100%. In some instances, solvent levels are reduced by at most about 10%, 20%, 30%, 40%, 50%, 60%, 70%, 80%, 90%, or 100%. Solvent levels can be reduced below about 290 ppm, 280 ppm, 270 ppm, 260 ppm, 250 ppm, 240 ppm, 230 ppm, 220 ppm, 210 ppm, 200 ppm, 190 ppm, 180 ppm, 170 ppm, 160 ppm, 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, or 10 ppm of hexane. Solvent levels can be reduced below about 4000 ppm, 3900 ppm, 3800 ppm, 3700 ppm, 3600 ppm, 3500 ppm, 3400 ppm, 3300 ppm, 3200 ppm, 3100 ppm, 3000 ppm, 2900 ppm, 2800 ppm, 2700 ppm, 2600 ppm, 2500 ppm, 2400 ppm, 2300 ppm, 2200 ppm, 2100 ppm, 2000 ppm, 1900 ppm, 1800 ppm, 1700 ppm, 1600 ppm, 1500 ppm, 1400 ppm, 1300 ppm, 1200 ppm, 1100 ppm, 1000 ppm, 900 ppm, 800 ppm, 700 ppm, 600 ppm, 500 ppm, 400 ppm, 300 ppm, 200 ppm, 100 ppm, 90 ppm, 80 ppm, 70 ppm, 60 ppm, 50 ppm, 40 ppm, 30 ppm, 20 ppm, or 10 ppm of cyclohexane. Solvent levels can be reduced below about 5000 ppm, 4900 ppm, 4800 ppm, 4700 ppm, 4600 ppm, 4500 ppm, 4400 ppm, 4300 ppm, 4200 ppm, 4100 ppm, 4000 ppm, 3900 ppm, 3800 ppm, 3700 ppm, 3600 ppm, 3500 ppm, 3400 ppm, 3300 ppm, 3200 ppm, 3100 ppm, 3000 ppm, 2900 ppm, 2800 ppm, 2700 ppm, 2600 ppm, 2500 ppm, 2400 ppm, 2300 ppm, 2200 ppm, 2100 ppm, 2000 ppm, 1900 ppm, 1800 ppm, 1700 ppm, 1600 ppm, 1500 ppm, 1400 ppm, 1300 ppm, 1200 ppm, 1100 ppm, 1000 ppm, 900 ppm, 800 ppm, 700 ppm, 600 ppm, 500 ppm, 400 ppm, 300 ppm, 200 ppm, 100 ppm, 90 ppm, 80 ppm, 70 ppm, 60 ppm, 50 ppm, 40 ppm, 30 ppm, 20 ppm, or 10 ppm of class III solvents (e.g., acetone and ethanol).

Methods of the present disclosure can reduce the loss on drying of a cantharidin preparation. For example, loss on drying (e.g., at 105° C. for 3 hours) can be less than or equal to about 2.1% 2%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1%.

Methods of the present disclosure can reduce the residue on ignition of a cantharidin preparation. For example, residue on ignition (e.g., at 750° C. for 5 hours) can be less than or equal to about 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1%.

Methods of the present disclosure can reduce the total plate count of a cantharidin preparation. For example, total plate count can be less than or equal to about 125, 120, 110, 100, 95, 90, 85, 80, 75, 70, 65, 60, 55, 50, 45, 40, 35, 30, 25, 20, 15, 10, 5, 4, 3, 2, or 1 colony forming units per gram (cfu/g). Methods of the present disclosure can reduce the yeast and/or mold content of a cantharidin preparation. For example, yeast and mold can be less than or equal to about 50, 45, 40, 35, 30, 25, 20, 15, 10, 5, 4, 3, 2, or 1 colony forming units per gram (cfu/g).

Analytical Methodologies

Cantharidin can be toxic. Cantharidin can have limited solubility. For example, cantharidin can have limited solubility in polar solvents. For example, cantharidin may be soluble up to at least 0.1, 0.5, 1, 1.5, 2, 2.5, 3, 3.5, 4, 4.5, 5, 5.5, 6, 6.5, 7, 7.5, 8, 8.5, 9, 9.5 or 10 or more mg/mL. Cantharidin may not readily absorb UV light. These limitations of cantharidin can limit detection of it and the detection of related impurities at high resolution.

The overall purity of cantharidin can be detected (e.g., analyzed) with chromatography, such as High Performance Liquid Chromatography (HPLC). Factors that can influence the sensitivity of an HPLC method can include, but are not limited to, stationary phase, mobile phase composition and pH and gradient, light sources and detectors used, instrumentation, temperature, and concentration of API as well as injection volume and speed.

Cantharidin and/or cantharidin-associated impurities can be detected (e.g., analyzed) in solution using UV-Vis spectroscopy. For example, UV-Vis light of a given wavelength can be directed into the solution (e.g., elution stream, elution fractions) and light emitted from the solution can be detected. The light that is emitted can be indicative of the purity of solution.

In some cases, cantharidin can absorb at about 180, 185, 190, 195, 200, 205, 210, 215, 220, 225, 226, 227, 228, 229, 230, 235, 240, 245, or 250 nanometers or more. In some instances, cantharidin has a maximum absorption at about 228 nm of light that is directed to the solution. Impurities in the cantharidin preparation can absorb poorly at a range of light that cantharidin can absorb. For example, impurities in the cantharidin preparation may absorb poorly at 228 nanometers. Cantharidin-associated impurities can be detected at about 180, 185, 190, 195, 200, 201, 202, 203, 204, 205, 206, 207, 208, 209, 210, 215, 220, 225, 226, 227, 228, 229, 230, 235, 240, 245, or 250 or more nanometers. In some instances, cantharidin-associated impurities can be detected at 205 nanometers.

The method may be performed such that chromatogram peaks corresponding to cantharidin and/or cantharidin-associated impurities are visible at a wavelength of less than about 230, 229, 228, 227, 226, 225, 224, 223, 222, 221, 220, 219, 218, 217, 216 215, 214, 213, 212, 211, 210, 209, 208, 207, 206, 205, 204, 203, 202, or 201 nanometers or less. In other words, the method can be performed at any wavelength such that the method adequately detects eluents (e.g., peaks in a chromatogram). Cantharidin and/or cantharidin-associated impurities may be visible at a wavelength of about 230, 229, 228, 227, 226, 225, 224, 223, 222, 221, 220, 219, 218, 217, 216 215, 214, 213, 212, 211, 210, 209, 208, 207, 206, 205, 204, 203, 202, or 201 nanometers or less.

Methods for monitoring wavelengths of light from a cantharidin solution can be used with other methods provided herein. For example, wavelengths of light from a cantharidin solution can be used to assess the effectiveness of recrystallization methods provided herein.

Highly Sensitive Analytical Methodologies for Directly Detecting Cantharidin and Associated Impurities The disclosure provides methods for directly detecting cantharidin and cantharidin-associated impurities in a solution having or suspected of having cantharidin and cantharidin-associated impurities. The method can have a limit of quantification. The limit of quantification can refer to at least 10 times the standard deviation of the noise level (e.g., blank, control). The limit of quantification can be at least 0.001%, 0.005%, 0.01%, 0.05%, 0.1%, 0.15%, 0.2%, 0.25%, or 0.3% or more. The limit of quantification can be at most 0.001%, 0.005%, 0.01%, 0.05%, 0.1%, 0.15%, 0.2%, 0.25%, or 0.3% or more. The limit of quantification can be about 0.05%.

The method can have a limit of detection. The limit of detection can refer to a signal about 3 times the standard deviation of the noise level (e.g., blank, control). The limit of detection for the methods of the disclosure can be at least 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% or more. The limit of detection for the methods of the disclosure can be at most 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1%. The limit of detection can be less than 0.02%. The limit of detection can be monitored at 205 nanometers (or other wavelengths disclosed herein). In other words, if the limit of detection is 0.02% it can be 0.02% at 205 nanometers (or other wavelengths disclosed herein).

Mobile Phases

The methods of the disclosure can comprise the use of chromatography, such as HPLC, for analyzing (e.g., detecting) cantharidin. The method can have a limit of quantification (LOQ) of 0.05%. The method can comprise a limit of detection of less than 0.02% at 205 nm, the wavelength which can allow for the optimum detection of cantharidin related impurities.

The method of the disclosure can comprise dissolving cantharidin material in an appropriate solvent or mixture of solvents at a predetermined concentration. The solvent can be a solvent or mixture of solvents in which cantharidin does not break down. Exemplary solvents can include DMSO, acetone, chloroform, diethyl ether, ethanol, methanol, and acetonitrile. In some instances, the solvent is acetonitrile. The concentration of cantharidin dissolved can be from 1, 2, 3, 4, 5, 6, 7, 8, 9, 10, 11, 12, 13, 14, 15, 16, 17, 18, 19, or 20 or more mg/mL. In some instances, the concentration of dissolved cantharidin is 8 mg/mL. In some instances, 8 mg/mL of cantharidin is dissolved in acetonitrile.

The method of the disclosure provides for analyzing (e.g., detecting) cantharidin with mobile phases (e.g., multiple solutions to move through a column). The first mobile phase can comprise water at a pH of least pH 1, 1.5, 2, 2.5, 3, 3.5, 4, 4.5, 5, 5.5, 6, 6.5, or 7 or more. The first mobile phase can comprise water at a pH of most pH 1, 1.5, 2, 2.5, 3, 3.5, 4, 4.5, 5, 5.5, 6, 6.5, or 7 or more. The mobile phase can comprise water at pH of 3. The pH of the first mobile phase can be adjusted with an acid. The pH of the second mobile phase can be adjusted with an acid. Exemplary acids can include, but are not limited to, hydrochloric acid, sulfuric acid, acetic acid, trifloric acid, any acid giving a pH of about 3, and phosphoric acid. In some instances, the first mobile phase is buffered with phosphoric acid. A first mobile phase (e.g., mobile phase A) can comprise pH 3 water buffered with phosphoric acid. The first or second mobile phase can be buffered. Exemplary buffers include, but are not limited to, TFA, methane sulphonic acid, phosphate, citrate, carbonate, formate, acetate, ammonia, borate, triethylamine, tris (hydroxymethyl) aminomethane, pyrrolidine.

A second mobile phase (e.g., mobile phase B) can comprise at least 60, 70, 80, 90, 95, or 100% of an organic solvent. In some instances, the second mobile phase comprises 100% organic solvent. Organic solvents suitable for the second mobile phase can include, but are not limited to, acetonitrile, methanol, and tetrahydrofuran, propanol. In some instances, the second mobile phase comprises 100% acetonitrile.

In some instances, the methods of the disclosure provide for using two mobile phases: a first phase comprising pH 3 water buffered with phosphoric acid and a second phase comprising 100% acetonitrile.

Detection Apparatus and Detection Method

The methods of the disclosure provide for performing chromatography to analyze (e.g., detect) cantharidin. Exemplary types of chromatography can include, HPLC, Reverse-Phase HPLC, FPLC, LC-MS (liquid chromatography-mass spectrometry), LC-MS/MS, GC-MS (gas-chromatography-mass spectrometry), ion exchange chromatography, and size exclusion chromatography. In some instances, the methods of the disclosure provide for detection of cantharidin using HPLC. The methods of the disclosure can provide for detection using methods such as electrophoresis.

An HPLC chromatography apparatus can include at least the following components: a column, packed with a suitable stationary phase, a mobile phase, a pump for forcing the mobile phase through the column under pressure, and a detector for detecting the presence of compounds eluting off of the column. The apparatus can include one or more units for providing for gradient elution, where the solvent system is varied during the detection.

A HPLC chromatography apparatus can comprise a stationary phase. A stationary phase can comprise solid supports. For example, silica particles can be solid supports in a stationary phase. Solid supports in the stationary phase can be functionalized (e.g., with silanes). Silica particles can be coupled with silanes with coupling agents such as agents with a general formula of $EtOSiR_1R_2R_3$ or $ClSiR_1R_2R_3$, where R represents organic groups, which can differ from each, though in some cases some or all can be the same. A silane group can be $Si(CH_3)_2(C_{18}H_{37})$, where $C_{18}H_{37}$, octadecyl group, yields a hydrophobic surface. In some instances, the stationary phase is a C18 column.

In some embodiments, the method of the disclosure comprises detecting a cantharidin extract using a combined HPLC-MS technique in which the HPLC separation is performed in-line with the MS analysis. Specifically, the HPLC apparatus can be directly connected to the mass spectrometer, wherein the mass spectrometer directly receives the separated products from the HPLC column. The methods of the disclosure can employ a combination of high-temperature column RP-HPLC separation with the use of a high percentage of a water miscible organic solvent.

The combined use of a reversed-phase HPLC method with UV and MS detection for analyzing (e.g., monitoring) the purity of the eluents can be used. The RP-HPLC (reverse phase-HPLC) method can use high column temperatures, one or more mobile phases, and silica stationary phases with alkyl chains from C3 to C18, which may or may not comprise further derivatization with e.g., cyano and diphenyl derivatives The HPLC purification method of the disclosure can be used in combination with UV-Vis (also, UV/VIS) spectrometry. The method can comprise coordinating UV/VIS absorbency values of a stream of eluate from a chromatographic column, the eluate comprising cantharidin and/or cantharidin-associate impurities. Such a method may comprise the following steps: (a) the eluate stream can be passed continuously through a UV/VIS spectrophotometer adapted to continuously monitor the absorbency values of the eluate stream. (b) The eluate stream exiting the UV/VIS spectrophotometer can be conveyed to a pair of parallel metering valves. (c) The parallel metering valves can be adjusted so that a portion of the eluate from the UV/VIS spectrophotometer is directed to a stream splitter and the remaining portion of such eluate is directed to a waste disposal. The UV/VIS absorbency values can be graphically depicted on a chromatogram.

In some instances, the stationary phase comprises a gas chromatography system or a combined gas chromatography and mass spectrometry system. A gas chromatography plus mass spectrometer (GC/MS) system can include a gas chromatograph, a mass spectrometer, and a computer interface to both of them. The mass spectrometer can include an ion source with an electron emission filament which can be damaged if on during the time a solvent peak is eluting from the chromatograph. The filament can be regulated to provide a constant emission rate by feedback which causes a current source to compensate deviations from a desired emission level. When a solvent peak begins to elute, the concomitant sudden cooling of the filament can be sensitively reflected in the feedback to the current source. A comparator AC-coupled to the current source input can be used in shutting off the current source when the emission current abruptly drops. A computer controller can reactivate the filament in response to a decrease in ambient pressure or elapse of a predetermined duration so that component peaks following the solvent peak can be analyzed. A gas chromatograph separates the components of a mixture in solution by volatizing the components of the solution into a carrier gas stream which is passing over a liquid stationary phase. This process takes place in a packed or capillary chromatography column.

The methods of the disclosure provide for using a flow rate of the phases and extract through the stationary phase. The flow rate can be at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 microliters/minute or more. The flow rate can be at most 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 microliters/minute or more. In some instances, the flow rate is about 1 microliter/minute.

The methods of the disclosure can be performed at any suitable temperature. The temperature can be at least 4, 10, 15, 20, 25, 26, 27, 28, 29, 30, 31, 32, 33, or 34° C. The temperature can be at most 4, 10, 15, 20, 25, 26, 27, 28, 29, 30, 31, 32, 33, or 34° C. In some instances, the temperature is about 30° C.

The methods of the disclosure provide for a detection wavelength to detect impurities in the cantharidin preparation. The detection wavelength can be at least 190, 195, 200, 201, 202, 203, 204, 205, 206, 207, 208, 209, 210, or 215 nanometers or more. The detection wavelength can be at most 190, 195, 200, 201, 202, 203, 204, 205, 206, 207, 208, 209, 210, or 215 nanometers or more. In some instances, the detection wavelength is 205 nanometers.

The detection method of the disclosure can be performed with a gradient. For example, the gradient can comprise 5, 10, 15, 20, 25, 30, 35, 40, 45, 50, 55, 60, 65, 70, 76, 80, 85, 90, 95 or 100% of the first mobile phase (e.g., mobile phase A) and 5, 10, 15, 20, 25, 30, 35, 40, 45, 50, 55, 60, 65, 70, 76, 80, 85, 90, 95 or 100% of the second mobile phase (e.g., mobile phase B). In some instances, a gradient of 85% phase A and 15% phase B is used initially and this is then set to run at 10% A and 90% B upon injection and for the remainder of the protocol.

The detection protocol can performed for at least 5, 10, 15, 20, 25, 30, 35, 40, or 45 or more minutes. The detection protocol can performed for at most 5, 10, 15, 20, 25, 30, 35, 40, or 45 or more minutes. In some instances, the detection protocol is performed for 17 minutes. Data is recorded for the length of the detection protocol. FIG. 2 illustrates one example of the HPLC method of the disclosure.

Methodologies for Preparing Drug Products and for Detection of Cantharidin and Associated Impurities The present disclosure provides methods for preparing drug products from material having or suspected of having cantharidin and cantharidin-associated impurities into forms capable of being analyzed with analytical methodologies, including highly-sensitive analytical methodologies described herein. Drug products can contain excipients that are incompatible with analytical methodologies and which may need to be removed or reduced in order for the methodologies to be functional. Some incompatible excipients can include materials such as film-formers, polymers, plasticizers, or thickeners. Incompatible excipients can include nitrocellulose, nitrocellulose derivatives, polyvinyl pyrrolidone, hydroxypropylmethycellulose, hydroxypropyl cellulose, carboxymethylcellulose, fumed silica, castor oil or camphor. Other excipients such as dyes can absorb strongly in the UV or visible spectrum and can interfere with analysis.

A drug product can be mixed with a diluent. This diluent can be, without limitation, ethyl acetate, isopropyl acetate, tetrahydrofuran, dioxane, diisopropyl ether, tert-butyl methyl ether, methylene chloride, ethylene dichloride, toluene, 1,2-dimethoxyethane, hexane, cyclohexane, acetone, acetonitrile, methanol, or water. This diluent can be a combination of diluents or solvents. The diluent can be a mixture of acetonitrile and water. In some instances the diluent can be a 800:200 v/v mixture of acetonitrile:water. In some instances, the diluent can be added in a ratio of 3 mL for every gram of drug product.

A drug product can form a precipitate when the diluent is added and/or mixed. This precipitate can interfere with analysis of the drug product, for example by clogging the equipment, or by interfering with the readings and giving misleading results. It can be desirable to remove the precipitate while leaving the cantharidin and cantharidin associated impurities in solution. The drug product and diluent can be mixed or vortexed. The drug product and diluent can be mixed for at least about 5, 10, 20, 30, 45, 60, 120, 180, 240 or 300 seconds or more. In some instances, additional diluent can be mixed in, and the sample can be mixed or vortexed for an additional period of time.

A precipitate may be removed. For example, a precipitate can be removed by letting the sample sit for an extended period of time. A precipitate can be removed by centrifugation. Centrifugation can take place for at least 1, 2, 3, 4, 5, 10, 15, 30, or 60 minutes or more. Centrifugation can take place at greater than or equal to about 1, 10, 100, 1,000, 2,000, 5,000, 10,000, 15,000, 20,000, 50,000 or 100,000×g.

The resulting supernatant after removing precipitate can be used with analytical methods, such as those discussed herein, in order to get an accurate measurement of the concentration, purity and/or stability of a drug product having or suspected of having cantharidin and cantharidin-associated impurities. Table 2 illustrates one example of a drug product preparation method of the disclosure.

TABLE 2

Drug product preparation method.

| Step | Observation |
| --- | --- |
| Weigh 1 g of drug product into a 5 mL volumetric flask | |
| Add 3 mL of room temperature diluent | Precipitate will form |
| Mix by vortex for 30 seconds | Sample completely dispersed |
| Dilute sample to volume with diluent and mix well by vortex | Sample completely dispersed |
| Centrifuge an aliquot for 10 minutes at 16,000 × g | A pellet should form |
| Immediately transfer the supernatant to a vial | Sample should be free of precipitate |

Purification using Recrystallization

The present disclosure provides methods for recrystallizing cantharidin. Recrystallization can be used to purify cantharidin from a cantharidin product comprising cantharidin-associated impurities. Such methods can comprise the use solvents with high cantharidin solubility at one temperature but lower solubility at lower temperatures to eliminate or reduce specific impurities present in cantharidin products. A specific impurity can refer to a non-cantharidin impurity. For example, the recrystallization method can comprise dissolving a cantharidin extract comprising cantharidin-associated impurities in a suitable solvent, heating the solvent, and then cooling the solvent. Cooling can result in increased precipitation of cantharidin and reduce precipitation of cantharidin-associated impurities (e.g., they stay in solution). The precipitated cantharidin can have a higher concentration than the cantharidin in solution (e.g., dissolved cantharidin).

Recrystallization can result in a purity greater than or equal to about 50, 60, 70, 80, 95, 95, 98, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100%. Recrystallization can result in a purity of at most about 50, 60, 70, 80, 90, 95, 98, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, 99.95, 99.99 or 100%. As used herein, "purity" can refer to the percentage of cantharidin versus other products in a cantharidin extract purified by the methods of the disclosure. For example, an extract that is 99.9% pure can mean that 0.1% of the extract is impurities.

The method can reduce the total impurities below 5%, 2%, 1%, 0.5%, 0.1% or 0.01% or less. The method can reduce each specific impurity below 1.0%, 0.5%, 0.25%, 0.20%, 0.15%, 0.10%, 0.05%, 0.01%, or less The method can comprise a yield greater than or equal to 25%, 50%, 70%, 75%, 80%, 85%, 90%, 95% or 99%.

The method can reduce specific impurities by at least 20%, 30%, 40%, 50%, 60%, 70%, 80%, or 90% or more. The method can reduce specific impurities by at most 20%, 30%, 40%, 50%, 60%, 70%, 80%, or 90% or more. For example, the concentration of the cantharidin-associated impurity with a RRT of 0.63 can be reduced by about 86% (from 0.37 to about 0.05%). The concentration of the cantharidin-associated impurity with a RRT of 1.19 can be reduced by about 80% (from 0.28% to below 0.05%). The concentration of the cantharidin-associated impurity with a RRT of 1.26 can be reduced by about 81% (from 0.26% to below 0.05%). Recrystallization can reduce cantharidin-associated impurities to below ICH detection limits.

In some cases, the method may not reduce total impurities but may reduce specific impurities. For example, the method may not substantially reduce total impurities but may reduce specific impurities by at least 20%, 30%, 40%, 50%, 60%, 70%, 80%, or 90% or more. The method may not substantially reduce total impurities but may reduce specific impurities by at most 20%, 30%, 40%, 50%, 60%, 70%, 80%, or 90% or more. The method may not substantially reduce total impurities but may reduce a specific impurity below 0.05%. The method may not substantially reduce total impurities but may reduce a specific impurity below at least about 1%, 0.5%, 0.1%, 0.05%, or 0.01%. The method may not substantially reduce total impurities but may reduce a specific impurity below at most about 1%, 0.5%, 0.1%, 0.05%, or 0.01%. The method may not substantially reduce total impurities but may reduce a specific impurity below ICH detection limits.

Recrystallization can result in crystal forms that are the same or different from the starting material. For example, recrystallization can result in crystalline material including, but not limited to needles, prisms or plates. Recrystallization can result in a crystalline product of cantharidin wherein the concentration of water in the recrystallized product is less than about 1%, 0.9%, 0.8%, 0.7%, 0.6%, 0.5%, 0.4%, 0.3%, 0.2%, or 0.1% or less. Recrystallization can result in an increase in crystal size, a reduction of very small or crushed crystals, or can result in a more uniform crystal size distribution. Cantharidin crystals can be between 1 and 2000 μm in length. Recrystallization can result in the reduction of smaller crystals that may easily aerosolize. Recrystallization can result in a preparation with more uniform crystal size distribution.

Recrystallization can result in the formation of new polymorphs that have improved solubility and/or stability. The methods of the disclosure can result in a product that is more soluble than the starting material. The product can be at least 1%, 5%, 10%, 20%, 50%, 100%, 200%, 500% or 1000% or more soluble than the starting material. Recrystallization can result in a crystalline product of cantharidin with improved stability.

Recrystallization can result in crystal forms that have higher melting points than the starting material. Recrystallization can result in a crystalline product of cantharidin with a peak melting point of at least about 212, 213, 214, 215, 216, 217, 217.1, 217.2, 217.3, 217.4, 217.5, 217.6, 217.7, 217.8, 217.9 or 218° C. Recrystallization can result in crystal forms that have higher onset of melting points than the starting material. Recrystallization can result in a crystalline product of cantharidin with an onset of melting point of at least about 212, 213, 214, 215, 216, 217, 217.1, 217.2, 217.3, 217.4, 217.5, 217.6, 217.7, 217.8, 217.9 or 218° C. Melting point (e.g., peak melting point, onset of melting) can be used as an indication of purity.

Recrystallization can reduce the concentration of catalysts, by-products, or chemicals used in the initial purification or synthesis. For example, recrystallization can reduce the concentration or amount of catalyst, by-products, or other chemicals from initial purification or synthesis by at least about 10%, 20%, 30%, 40%, 50%, 60%, 70%, 80%, 90%, 95%, 96%, 97%, 98%, 99%, 99.9%, 99.99%, or 99.999% compared to a composition prior to use of methods of the present disclosure Examples of catalysts include a Lewis Acid such as lithium perchlorate or a reducing agent such as Raney Nickel, platinum, palladium, platinum derivative, or palladium derivative.

The method of recrystallization can involve solubilizing a cantharidin product in 1, 10, 100, or 1000 or more of a suitable solvent or mixture of solvents. A suitable solvent can be a solvent that dissolves increasingly greater concentration of cantharidin at one temperature and less cantharidin at other temperatures. These solvents may include acetone, tetrahydrofuran, dichloromethane, dimethyl sulfoxide, ethanol, glycol ethers including but not limited to 2-ethoxyethanol, petroleum ether (benzene), anisol, toluene, ethyl acetate, isopropyl acetate, chloroform, diethyl ether, diisopropyl ether, tert-butyl methyl ether, ammonia, and N-methyl-2-pyrrolidone, ICH class III solvents such as acetic acid, acetone, 1-butanol, 2-butanol, butyl acetate, dimethyl sulfoxide, ethanol, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, and propyl acetate, or any combination thereof.

A suitable solvent can be any solvent where cantharidin is soluble at greater than 1, 2, 3, 4, 5, 6, 7, 8, 9, 10, 11, 12, 13, 14, or 15 g/L or more. In some instances, a suitable solvent is a solvent wherein cantharidin is soluble at greater than about 8 g/L.

Heating may be required to get the cantharidin to dissolve in the solvent. The dissolved cantharidin solution can be heated or left at room temperature to reduce the volume and concentrate the cantharidin. Heating can occur at about 50, 55, 60, 65, 70, 75, or 80° C. or more.

The solution can be cooled to help saturate the solution and aid with crystallization. Cooling can be performed at a temperature of about 10, 20, 30, 40, or 50° C. or more. A suitable anti-solvent can be added to further reduce the solubility of the cantharidin while keeping specific impurities in solution. Co-solvents or anti-solvents that lower the solubility of cantharidin but still solubilize specific impurities can include, water, heptane, hexane, pentane, ethanol, or any other solvent where cantharidin has solubility of less than 8 g/L. Some solvents, such as tetrahydrofuran and dichloromethane, may result in the instability and eventual breakdown of cantharidin when used at high enough concentration. The pH of each solution can be changed using a suitable chemical to increase or decrease the solubility of cantharidin and each specific impurity. These pH-modifying reagents can include but are not limited to hydrochloric acid, phosphoric acid, acetic acid, potassium hydroxide and sodium hydroxide.

The solution can be maintained at a suitable temperature to promote continued crystal formation. For example, the solution can be maintained at about 5, 10, 15, 20, 25, 30, 35, or 40° C. or more for at least about 0.5, 1, 1.5 or 2 or more hours. The solution can be maintained at about 30° C. for at least about 0.5, 1, 1.5, or 2 or more hours. The solution can be maintained at about 30° C. for about 1 hour.

The solution can be brought to a specific temperature and incubated to allow for the completion of crystallization. For example, the solution can be cooled to about 5, 10, 15, 20, 25 or 30° C. or more. The solution can be cooled at about 10° C. for about 2 hours.

The crystalline material can be removed, placed over a filter and washed with a suitable solvent. For example, the material can be washed in water, acetone, ethanol, methanol, heptane, hexane or pentane or any other solvent suitable for washing. The crystalline material can be dried (e.g., washed, lyophilized). The recrystallization process can result in a yield of at least 20%, 30%, 40%, 50%, 60%, 70%, 80%, 90%, or 100% cantharidin.

One non-limiting example of the recrystallization method is described in Table 3.

TABLE 3

Method of recrystallization.

| Step | Observations |
| --- | --- |
| 20 V of Acetone is added to the compound | Solubilization at 55° C. |
| Concentration to 10 V at 75° C. | Nucleation during concentration |
| Cooling at 30° C. | |
| Pouring 1 V of Water | To achieve a ratio 90/10(V/V) Acetone/Water |
| Hold 1 h at 30° C. | Consumption of supersaturation |
| Cooling at 10° C. | |
| Isotherm at 10° C. at least 2 h | Consumption of supersaturation |
| Washing with 2 V of Water | Good filtration |
| Drying at 50 +/− 5° C. under vacuum | Yield: 85% |

Purification using Sublimation

Cantharidin may sublime when heated to a suitable temperature at atmospheric pressure or under a vacuum. Sublimation is the process of a changing a solid compound directly to a gaseous vapor without converting the solid to a liquid in the process. The gaseous vapor can be produced at lower temperatures than it takes to burn the material containing the compound.

Because many cantharidin-associated impurities do not sublimate, this process can be used to purify cantharidin with high yield without the use of solvents or columns. To purify cantharidin using sublimation, the starting cantharidin extract or synthetic product can be placed in a suitable sublimation apparatus such as a glass flask or tube. The cantharidin extract can be heated while under a vacuum or at ambient pressure. The cantharidin in the cantharidin extract or synthetic product can be sublimed in a sublimation stream. A cooling surface (e.g., in the form of a "cold finger") can be used to collect the purified product. Fractions of sublimed and/or recrystallized cantharidin can be collected at various increasing temperatures. The fractions can be combined to create a final product. The final product may comprise a reduced amount of total impurities. Total impurities can be less than about 5%, 2%, 1%, 0.5%, 0.1% or 0.01% or less.

In some instances, the extract (e.g., starting material) that can comprise cantharidin and cantharidin-associated impurities can have a first concentration. Sublimed cantharidin and/or cantharidin in a sublimation stream (e.g., in the process of being sublimed) can have a second concentration, wherein the second concentration is greater than the first concentration (e.g., before sublimation occurs). The second concentration can be at least about 1, 2, 3, 4, 5, 6, 7, 8, 9, or 10-fold or more higher than the first concentration. In some instances, the second concentration is at most about 1, 2, 3, 4, 5, 6, 7, 8, 9, or 10-fold or more higher than the first concentration.

The cantharidin-associated impurities can sublime at a reduced rate compared to the cantharidin. The cantharidin-associated impurities can sublime at a rate of at least 10%, 20%, 30%, 40%, 50%, 60%, 70%, 80%, or 90% compared to the rate of sublimation of cantharidin. The cantharidin-associated impurities can sublime at a rate of at most 10%, 20%, 30%, 40%, 50%, 60%, 70%, 80%, or 90% compared to the rate of sublimation of cantharidin.

Sublimation can be performed at suitable temperatures. The temperature for sublimation can initiate at 70, 75, 80, 83, 84, 85, 90, 95, 100, 110, 120, 130 140, 150, 160, 170, 180, 190, 200, 210, 220, 230, 240, or 250° C. or higher. In some instances, the temperature for sublimation can initiate at about 84° C. or higher. In some instances a temperature gradient can be used to collect purified cantharidin to very high purity.

In one non-limiting example, cantharidin can be placed in glass test tube under ambient pressure and heated and maintained at about 93.3° C. Cantharidin may be collected from a 20° C. "cold finger," which may have cool water flowing therethrough.

The methods of the disclosure can be performed in combination or separately. For example, sublimation can be performed in combination with recrystallization. In another example, the method may only use recrystallization or only sublimation.

EXAMPLES

Example 1: Non-Optimized HPLC Method at 228 nm with a LOD of 0.12%

Figure 3:
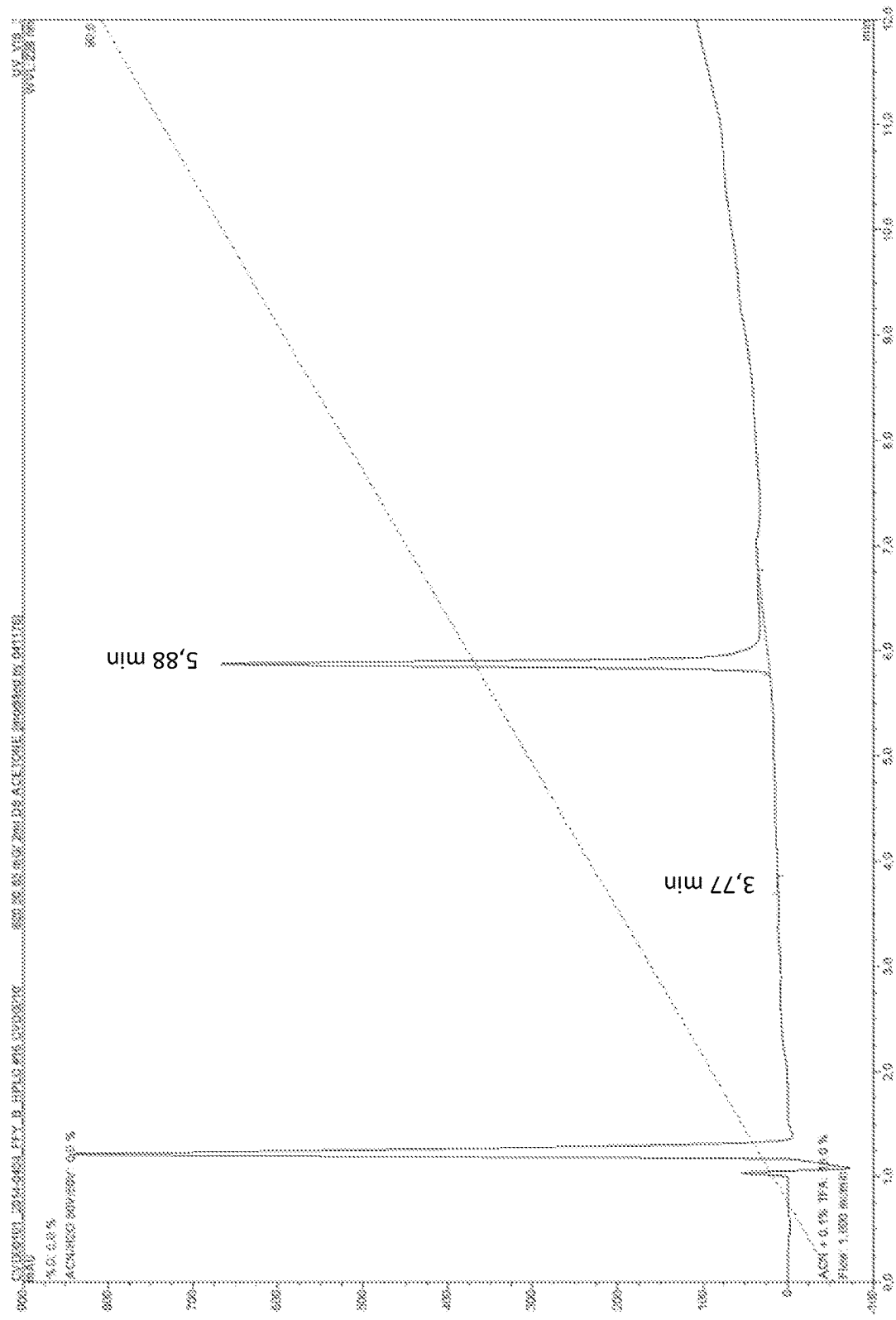
FIG. 3 depicts a chromatogram of an un-optimized chromatographic method with detection at 228 nanometers.

In this example, a cantharidin extract is prepared for HPLC detection at 228 nm. The HPLC conditions tested are 85% mobile phase A of water with 0.1% trifloric acid and 15% of mobile phase B of acetonitrile with 0.1% trifloric acid. The flow rate is 1 mL/minute. At 228 nm the LOQ is 0.12%. Only a single specific impurity is detected with a RRT of 0.64 (3.77 minutes). (see, e.g., FIG. 3 (x-axis from 0.0 to 12.0 minutes, y-axis from −100 to 900 mAU); the peak at t=3.77 is the cantharidin-associated impurity; the peak at t=5.88 is cantharidin).

Example 2: Non-Optimized HPLC Method at 205 nm with a LOQ of Greater than 0.30%

Figure 4:
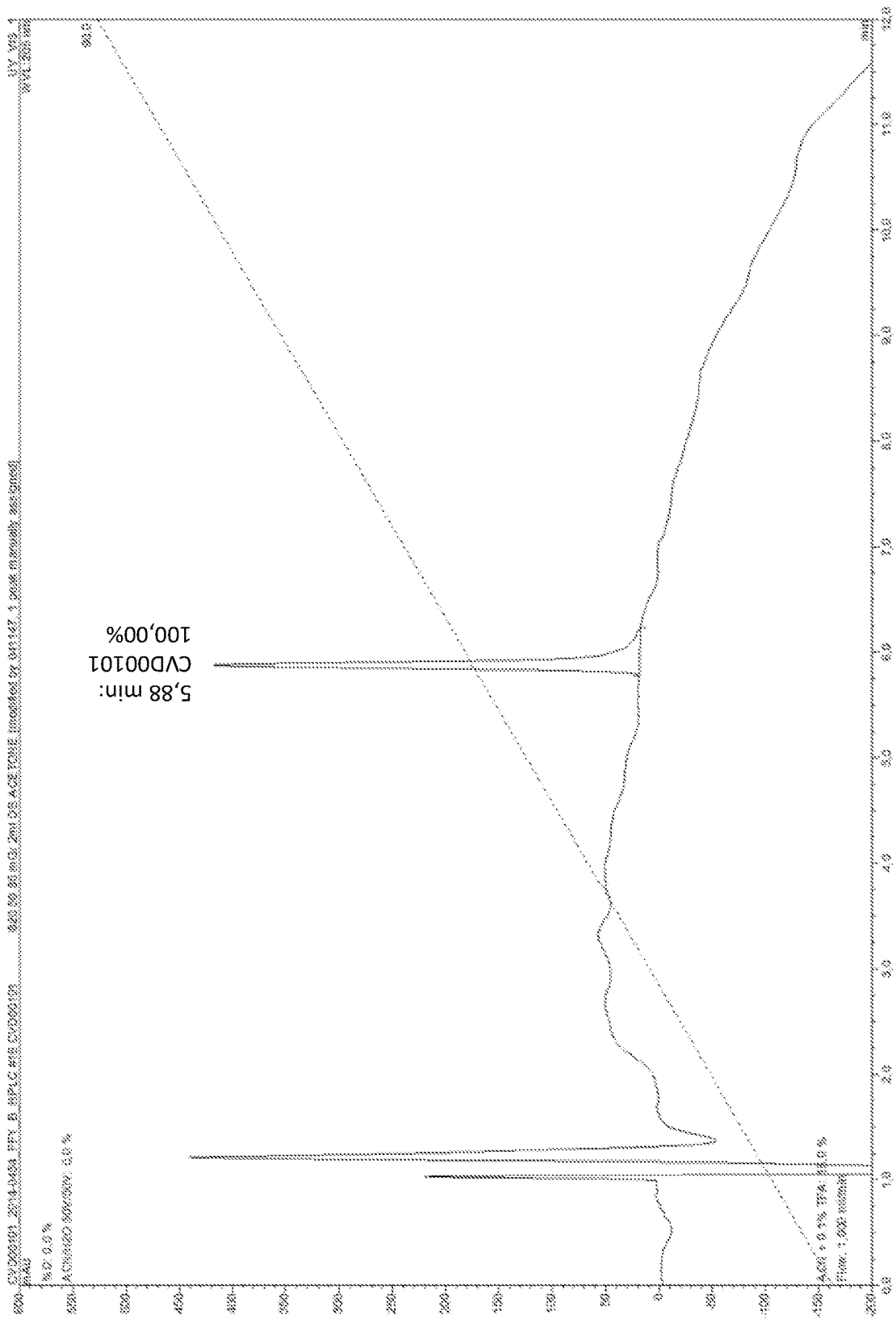
FIG. 4 depicts a chromatogram of an un-optimized chromatographic method with detection at 205 nanometers.

In this example, a cantharidin extract is prepared for HPLC with detection at 205 nm. The HPLC conditions tested are 85% mobile phase A of water with 0.1% trifloric acid and 15% of mobile phase B of acetonitrile with 0.1% trifloric acid. The flow rate is 1 mL/minute. At 205 nm the LOQ is greater than 0.30%. A single peak of cantharidin is seen at 5.88 minutes and no impurities are detected above 0.30%. (see, e.g., FIG. 4 (x-axis from 0.0 to 12.0 minutes, y-axis from −200 to 600 mAU)).

Example 3: Cantharidin Purification Using the HPLC Method of the Disclosure at 205 nm with an LOQ of 0.05%

In this example, a cantharidin extract is analyzed using the methods of the disclosure. The methods comprised the method outlined in FIG. 2. Specifically, the cantharidin extract is loaded onto a Kintetex C18 stationary phase column. The monitoring wavelength is 205 nanometers. The flow rate is 1 mL/minute. The method is performed at 30° C. The volume of cantharidin extract injected into the stationary phase is 10 microliters. The analysis time is 28 minutes with data being recorded from 0-17 minutes of the 28 minutes.

Figure 5:
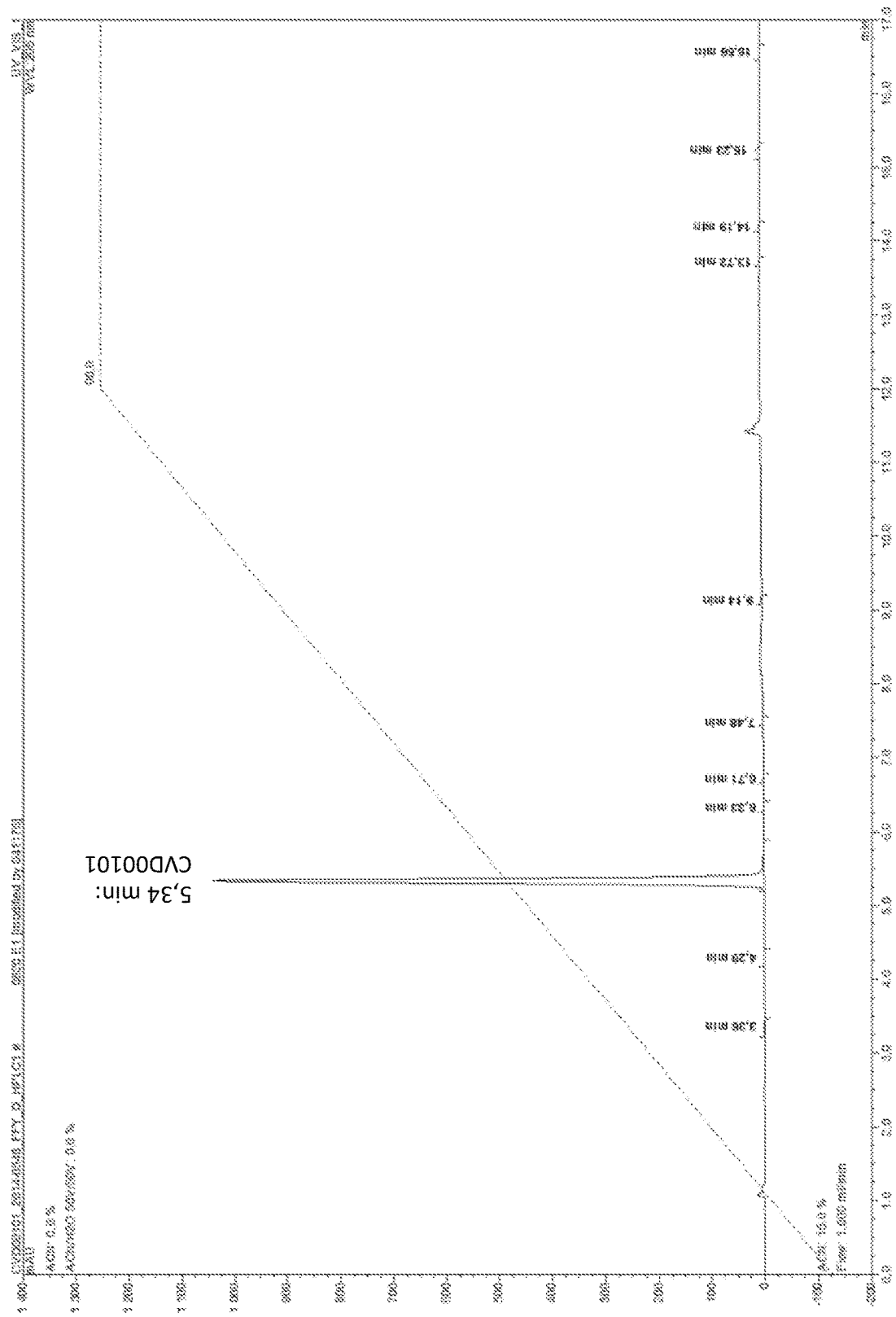
FIG. 5 depicts a chromatogram of an optimized chromatographic method of the disclosure with detection at 205 nanometers.

The stationary phase is washed with a gradient of mobile phase A and mobile phase B. At time zero the gradient comprises 85% mobile phase A and 15% mobile phase B. From time 12 minutes to 17 minutes, the gradient comprises 90% mobile phase A and 10% mobile phase B. From time 18 minutes to 28 minutes the gradient comprises 85% mobile phase A and 15% mobile phase B. Mobile phase A comprises water buffered to pH 3 with phosphoric acid. Mobile phase B comprises 100% acetonitrile. The concentration of extract injected is 8 mg/mL. The washing method is analyzed at 205 nanometers, and eluents coming off the stationary phased are graphically depicted (see, e.g., FIG. 5 (x-axis from 0.0 to 17.0 minutes, y-axis from −200 to 1400 mAU)). At least 10 impurities (3.36 min, 4.29 min, 6.33 min, 6.71 min, 7.48 min, 9.14 min, 13.72 min, 14.19 min, 15.23 min, 16.56 min), as well as cantharidin (5.34 min) are detected. Each peak corresponds to an impurity. (see, e.g., FIG. 5).

Example 4: Comparison of Method of the Disclosure with Chinese Pharmacopoeia Method This example compares cantharidin purification using the HPLC method of the disclosure and previous methods (e.g., Chinese Pharmacopoeia Method, as described in CN102268006, and The Chinese Pharmacopoeia Method 2010). Many impurities are not detected with the Chinese Pharmacopoeia method, but are detected with the methods of the disclosure. Table 4 shows the amount of impurities detected over three batches of cantharidin extract.

TABLE 4

Comparison of purification methods

| Cantharidin Extract Lot | Total Impurities Detected with Chinese Pharmacopoeia Method | Total Impurities Detected with New Method |
| --- | --- | --- |
| Lot # 1 | 0.8% | 1.1% |
| Lot # 2 | 0.8% | 1.4% |
| Lot # 3 | 0.4% | 1.8% |

The purified cantharidin (e.g., incoming cantharidin) is recrystallized. The recrystallized cantharidin is compared to the incoming cantharidin (e.g., before recrystallization) to determine how much recrystallization improved purity. The impurity profile of the incoming and recrystallized material from two distinct lots of cantharidin was analyzed with the HPLC method of the disclosure at 205 nm before and after recrystallization. A first batch (i.e., batch 820) changes from 98.6% to 99.93% pure. A second batch (i.e., batch 170) changes from 98.2% to 99.90% pure. Elution times are calculated by multiplying 5.34 minutes (cantharidin)×RRT. For example impurity RRT 0.53 has a retention time of 2.83 minutes (as calculated by 0.53×3.34 minutes). RRT can be a more accurate measurement as the retention time of cantharidin can change depending on the preparation.

Recrystallization is performed to increase the purity of the purified eluent of cantharidin. Recrystallization increases the purity of cantharidin to greater than or equal to 99.90%. Table 5 illustrates the change in purity of cantharidin-associated impurities before and after recrystallization.

TABLE 5

Recrystallization method can bring purity to over 99.9%.

| | Batch Number | | | |
| --- | --- | --- | --- | --- |
| Tests | Incoming 820 | Recrystallized 820 | Incoming 170 | Recrystallized 170 |
| Related substances (HPLC) (205 nm) | 1.4 | 0.07 | 1.8 | 0.10 |
| Sum of imp. (%) | | | | |
| RRT 0.53 | — | — | 0.14 | — |
| RRT 0.63 | 0.21 | — | 0.37 | 0.05 |
| RRT 0.71 | — | — | 0.14 | — |
| RRT 0.72 | — | — | 0.10 | — |
| RRT 0.75 | — | — | 0.08 | — |
| RRT 1.19 | <0.05 | — | 0.28 | — |
| RRT 1.26 | <0.05 | — | 0.26 | 0.05 |
| RRT 1.30 | <0.05 | — | 0.06 | — |
| RRT 1.42 | 0.08 | — | 0.17 | — |
| RRT 1.71 | 0.11 | — | 0.07 | — |
| RRT 1.92 | — | — | 0.09 | — |
| RRT 2.66 | 0.11 | — | <0.05 | — |
| RRT 2.85 | 0.81 | 0.07 | 0.18 | <0.05 |
| Any other | <0.05 | <0.05 | <0.05 | <0.05 |

Example 5: Purification of Cantharidin and Cantharidin Derivatives

This example describes the purification and detection of cantharidin derivatives. Cantharidin derivatives can comprise compounds which are very similar to cantharidin such as having a sulfur or sulfoxide group bound to them. The cantharidin derivatives are generated synthetically. One or more of the cantharidin derivatives have similar biological activity to cantharidin. Exemplary cantharidin derivatives are shown in FIG. 6.

A cantharidin derivative extract (e.g., comprising the cantharidin derivative) is heated in an appropriate solvent to dissolve the extract. The cantharidin derivative extract is cooled. The cantharidin derivative precipitates from the solution. The precipitated cantharidin derivative is washed and dried. The washed and dried cantharidin derivative is analyzed using a Kintetex C18 stationary phase column. The monitoring wavelength is 205 nanometers. The flow rate is 1 mL/minute. The method is performed at 30° C. The volume of cantharidin derivative extract injected into the stationary phase is 10 microliters. The analysis time is 28 minutes with data being recorded from 0-17 minutes of the 28 minutes.

The stationary phase is washed with a gradient of mobile phase A and mobile phase B. A time zero the gradient comprises 85% mobile phase A and 15% mobile phase B. From time 12-17 the gradient comprises 90% mobile phase A and 10% mobile phase B. From time 18-28 the gradient comprises 85% mobile phase A and 15% mobile phase B. Mobile phase A is comprised of water buffered to pH 3 with phosphoric acid. Mobile phase B comprises 100% acetonitrile. The concentration of extract injected is 8 mg/mL. The washing method is analyzed at 205 nanometers.

Example 6: Increased Melting Point of Recrystallized Cantharidin

Figure 7:
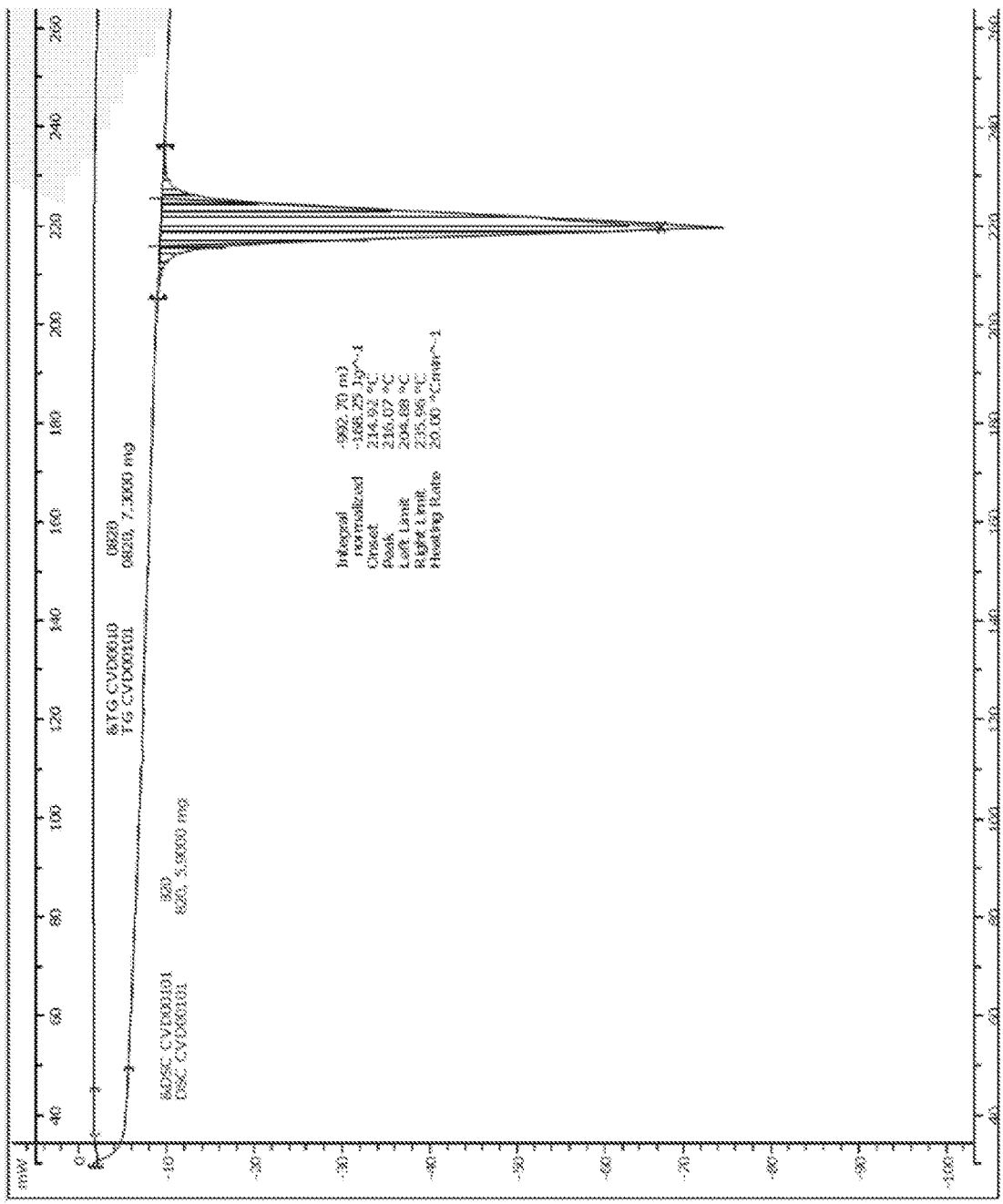
FIG. 7 depicts the melting point of a batch of crude cantharidin.
Figure 8:
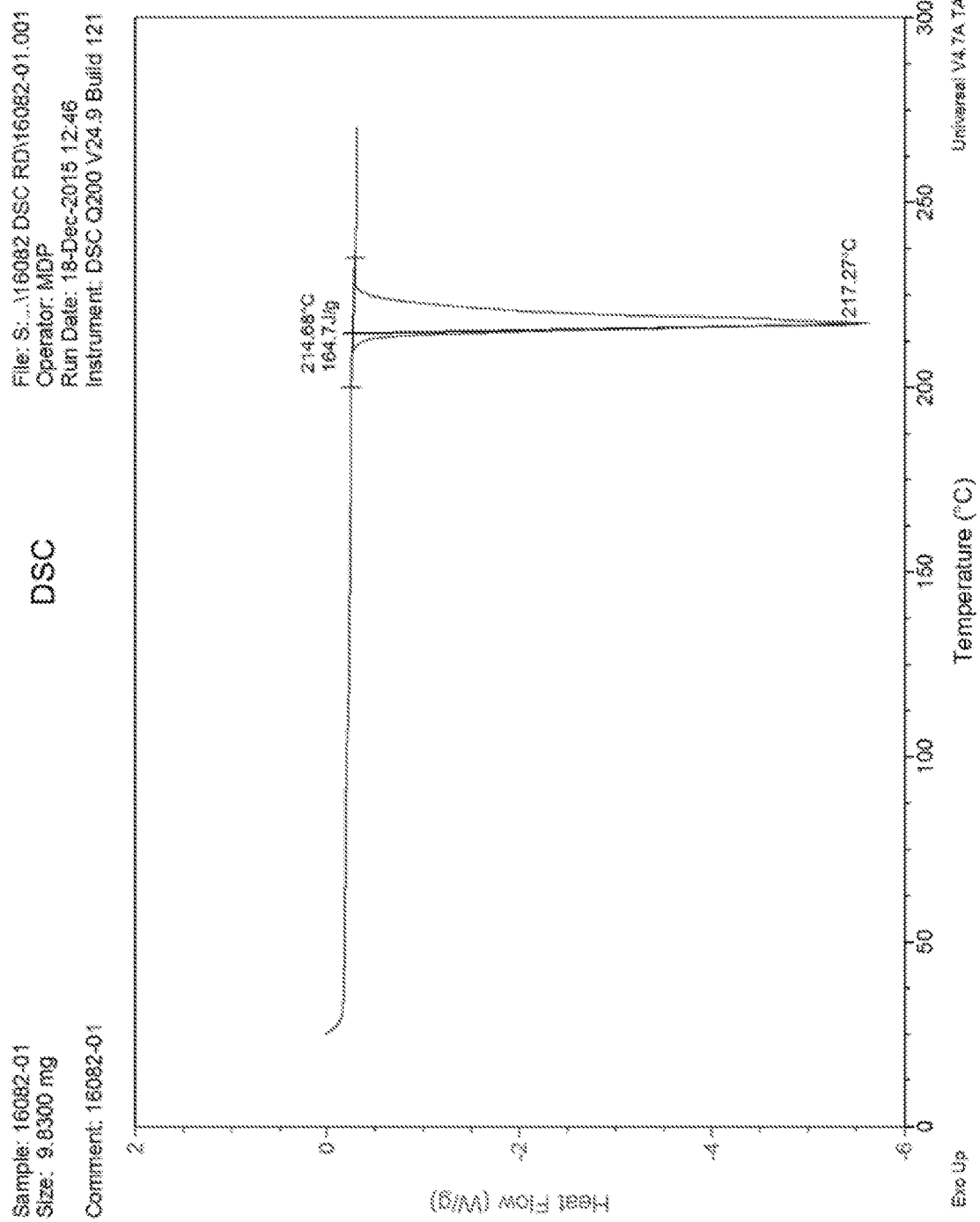
FIG. 8 depicts the melting point of a batch of recrystallized cantharidin.

This example demonstrates that recrystallized cantharidin can have a higher melting point than the initial cantharidin material. Crude cantharidin with a purity of 98.6% was analyzed by differential scanning calorimetry (DSC) analysis and found to have an onset of melting at 214.92° C. and a peak melting point of 216.07° C. (see, e.g., FIG. 7 (x-axis from 40 to 260° C., y-axis from −100 to 0 mW)). Recrystallized cantharidin with a purity of greater than 99.9% has an onset of melting at 214.68° C. and a peak melting point of 217.27° C. as shown by DSC analysis (see, e.g., FIG. 8 (x-axis from 0 to 300° C., y-axis from −6 to 2 W/g)).

Example 7: Purification of Crude Cantharidin

Figure 9A:
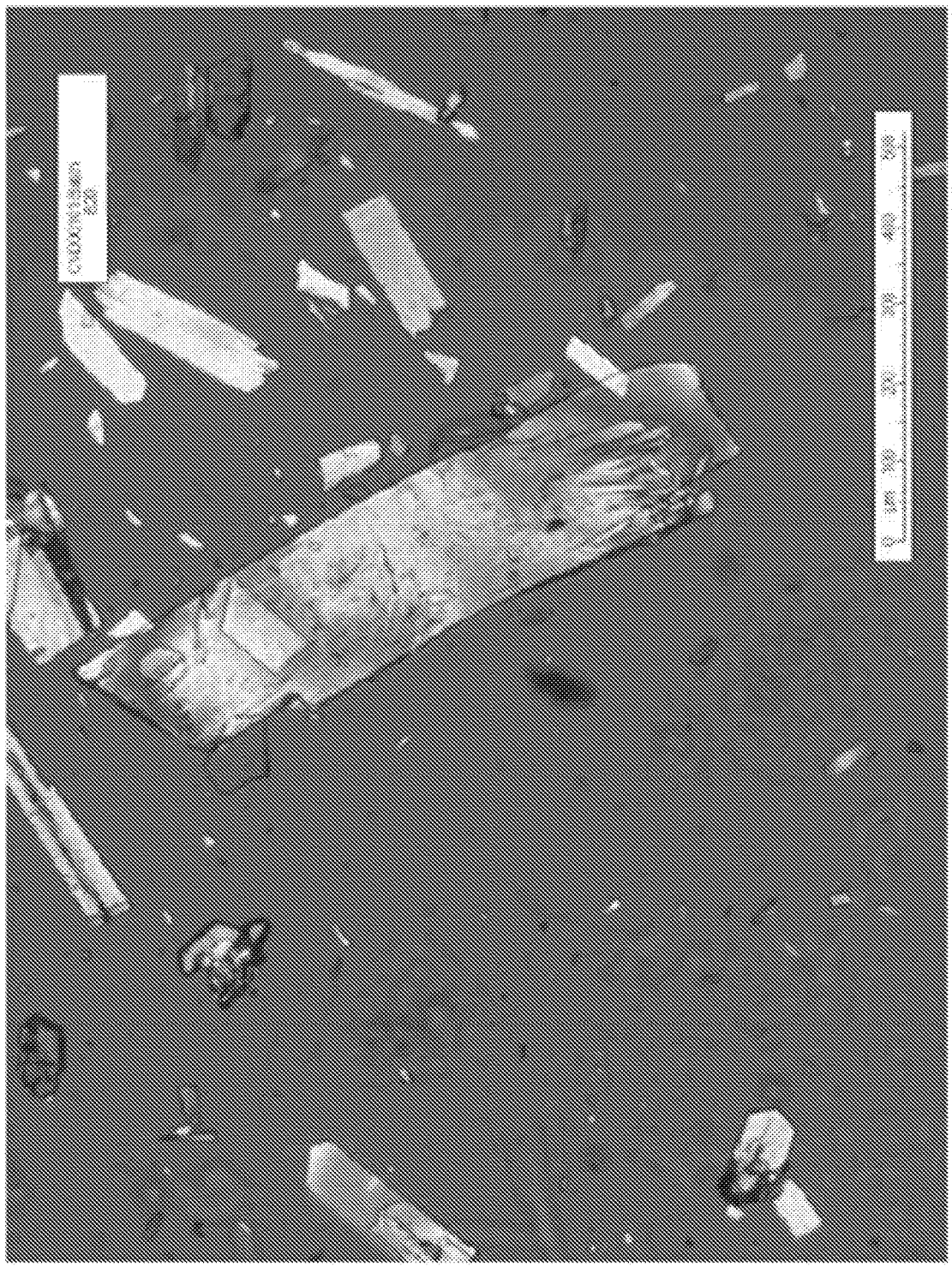
FIG. 9A shows an optical microscopy image of a crude cantharidin preparation.
Figure 9B:
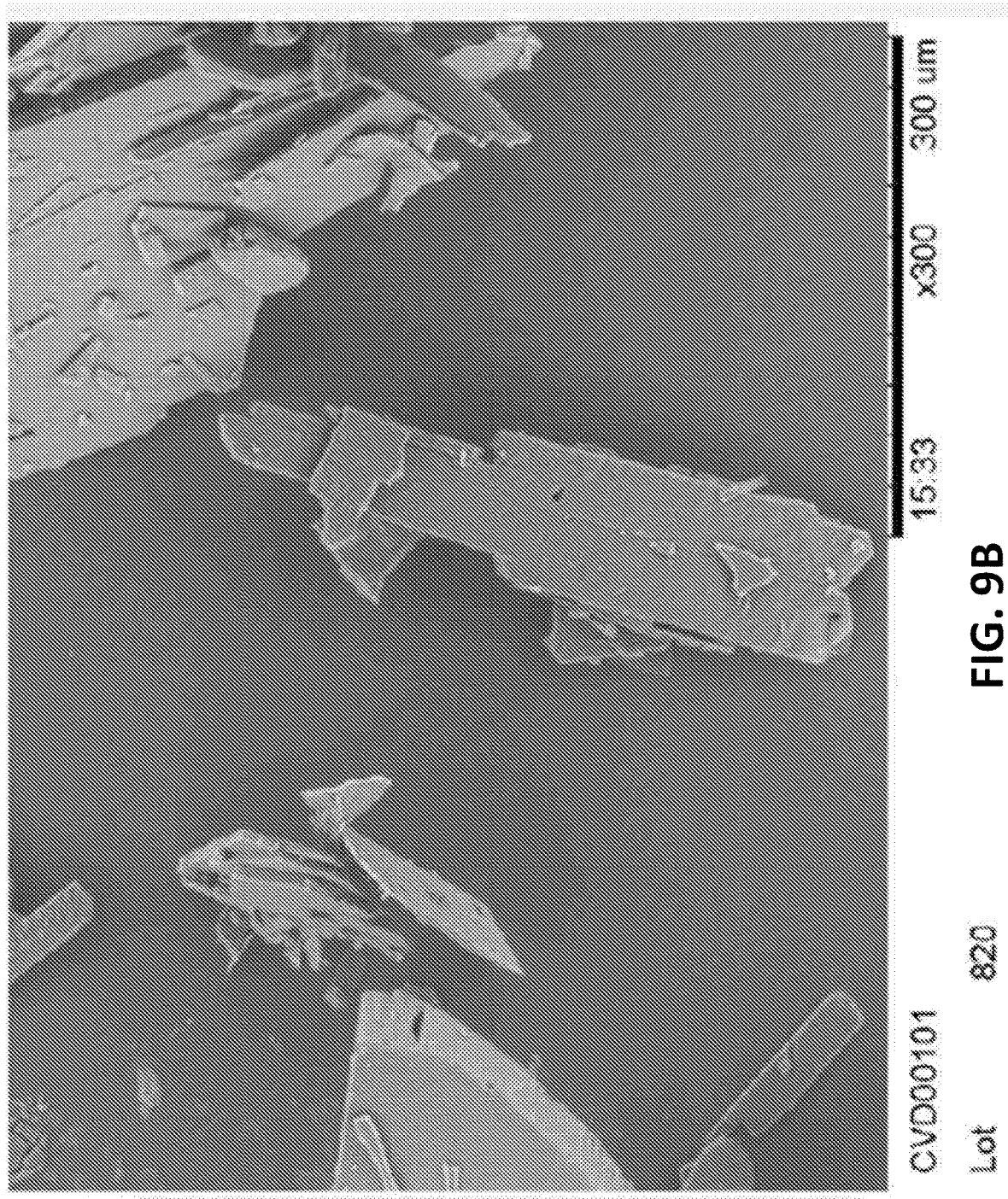
FIG. 9B shows a scanning electron microscope image of a crude cantharidin preparation.

This example demonstrates, among other things, the improvements to properties of cantharidin preparations that can be achieved by methods of the current disclosure. A crude cantharidin preparation, described in Table 6, was obtained. Analysis of the crude cantharidin concluded that it conformed to specifications, and when properly stored in a cool and dry place away from strong light and heat, it may have a shelf life of 3 years. FIG. 9A shows an optical microscopy image (obj. ×4, 500 µm scale bar) of a similar crude cantharidin preparation (batch 820). FIG. 9B shows a scanning electron microscope image (G×300, 300 µm scale bar) of a crude cantharidin preparation (batch 820). The product exhibited a platelet habit with the presence of big and fine particles, indicating a polymodal particle size distribution. FIG. 10 shows an X-ray Powder Diffraction (XRPD) analysis pattern of a crude cantharidin preparation (batch 820), showing peaks at 14.351, 15.137, 16.156, 17.711, 27.034, 28.722, 32.446, 32.678, and 35.217 [°].

TABLE 6

Crude cantharidin properties.

| Product Name | Cantharidin | Batch Number | 820 |
|---|---|---|---|
| Quantity | 500 G | Animal Source | *Mylabris Cichorii* L. |
| Manufacture Date | 2014 Mar. 25 | Used Part | dry bugs |
| Analysis Date | 2014 Mar. 30 | Exp Date | 2017 Mar. 24 |

| ANALYSIS ITEM | SPECIFICATION | RESULT | METHOD |
|---|---|---|---|
| Appearance | white crystal | Complies | Visual |
| Odor | Characteristic | Complies | Characteristic |
| Sieve Analysis | 100% pass 80 mesh | Complies | 80 mesh screen |
| Loss on Drying | ≤5.0% | 2.12% | 105° C./3 hrs |
| Residue on Ignition | ≤5.0% | 3.09% | 750° C./5 hrs |
| Extract Solvent | Ethanol and water | Complies | |
| Heavy Metal | <20 ppm | Complies | AAS |
| Arsenic (As) | <2 ppm | Complies | AAS |
| Residual Solvents | Eur. Pharm. 2000 | Complies | GC |
| Total Plate Count | <10000 cfu/g | 125 cfu/g | CP2005 |
| Yeast & Mold | <1000 cfu/g | 50 cfu/g | CP2005 |
| *E. coli* | Negative | Complies | CP2005 |
| *Salmonella* | Negative | Complies | CP2005 |
| ID test | Complies | Complies | Thin layer chromatography |
| ASSAY Cantharidin | ≥99.0% | 99.20% | HPLC |

The crude material was then processed by recrystallization methods as disclosed herein, and analyzed for comparison to the crude starting material. Results from this analysis are shown in Table 7.

TABLE 7

Recrystallized cantharidin properties.

| Analysis Item | Crude Specification | Crude Measurement | Recrystallized Measurement |
|---|---|---|---|
| Crystal size | 80 mesh (177 µm) max size | Various sizes ranging from less than 10 µm to greater than 500 µm | unknown |
| Loss on drying Crude method: 105° C. for 3 hours Recrystallized method: water content (USP <921 Ic>) | Less than 5% | 2.12% | 0.04% |
| Residue on Ignition Crude method: 750° C. for 5 hours Recrystallized method: USP <281> | Less Than 5% | 3.09% | 1.1% |
| Heavy Metals | Less than 20 ppm | Less than 20 ppm | Unknown |
| Residual Solvent | Less than: 290 ppm hexane, 3880 ppm cyclohexane, 5000 ppm for class III solvents (acetone and ethanol) | Passes specification by Gas Chromatography | 1865 ppm of acetone |
| Total Plate Count | Less than 10,000 cfu/g | 125 cfu/g | Unknown |
| Yeast and Mold | Less than 1000 cfu/g | 50 cfu/g | Unknown |
| Arsenic (AAS Method) | Less than 2 ppm | Less than 2 ppm | Unknown |

Preparations (or formulations) of the present disclosure may be used to treat various ailments, such as warts, Molluscum contagiosum, Actinic keratosis, Seborrheic keratosis or other cutaneous hyper-proliferative disorders, such as those that have failed or have been recalcitrant to prior therapy. Such preparations may be used to treat a subject with cancer. For instance, a cantharidin preparation may be used to inhibit tumor growth and/or used to kill cancer cells directly. In some cases, such preparations may be used to kill cancer stem cells. In some cases, a cantharidin preparation may be used to treat benign cancerous lesions. For example, a cantharidin preparation may be used to kill cancer cells with a multidrug resistant phenotype. In some situations, norcantharidin, cantharidimide, or analogues of cantharidin may be utilized instead of cantharidin.

Cantharidin preparations (or formulations) of the present disclosure may have properties or characteristics, and delivered to a subject using approaches described, in Patent Cooperation Treaty Patent Publication No. WO/2015/027111 ("COMPOSITIONS, METHODS AND SYSTEMS FOR THE TREATMENT OF CUTANEOUS DISORDERS"), which is entirely incorporated herein by reference.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for purifying cantharidin, comprising the steps:
    (a) providing a first cantharidin preparation comprising cantharidin and a cantharidin-associated impurity;
    (b) dissolving said first cantharidin preparation in a solvent by heating to generate a solution comprising cantharidin and the cantharidin-associated impurity; wherein the solvent is selected from the group consisting of acetone, methylethyl ketone, methylisobutyl ketone, tetrahydrofuran, a glycol ether, diethyl ether, diisopropyl ether, tert-butyl methyl ether, dichloromethane, chloroform, dimethyl sulfoxide, ethanol, petroleum ether, heptane, pentane, anisole, toluene, benzene, isopropyl acetate, butyl acetate, isobutyl acetate, methyl acetate, propyl acetate, acetic acid, ammonia, N-methyl-2-pyrrolidone, 1-butanol, 2-butanol, 3-methyl-1-butanol, 2-methyl-1-propanol, 1-pentanol, 1-propanol, 2-propanol, ethyl formate, formic acid, and mixtures thereof;
    (c) cooling said solution, thereby precipitating from said solution a second cantharidin preparation, wherein, during cooling, said second cantharidin preparation precipitates at a higher rate as compared to said cantharidin-associated impurity; and
    (d) adding an anti-solvent to the solution to further reduce the solubility of cantharidin in said solution while keeping said cantharidin-associated impurities in solution, wherein the anti-solvent is water.

2. The method of claim 1, wherein the solvent used in step (b) is acetone.

3. The method of claim 1, wherein the solution is heated to a temperature from about 50° C. to about 60° C. in step (b).

4. The method of claim 1, wherein the solution is heated to a temperature of about 55° C. in step (b).

5. The method of claim 1, wherein step (b) further comprises a step of concentrating the solution.

6. The method of claim 5, wherein the step of concentrating is carried out at a temperature of about 75° C.

7. The method of claim 1, wherein the solution is cooled to a temperature from about 20° C. to about 40° C. in step (c).

8. The method of claim 1, wherein the solution is cooled to a temperature of about 30° C. in step (c).

9. The method of claim 1, further comprising a step (e) of maintaining said solution of step (d) at a temperature to promote continued crystal formation.

10. The method of claim 9, further comprising a step (f) of cooling said solution to a temperature and maintaining the solution at that temperature.

11. The method of claim 10, further comprising a step (g) of filtering the second cantharidin preparation from said solution.

12. The method of claim 1, wherein the solvent used in step (b) is acetone; and water is added to the solution in step (d) to achieve a ratio of about 90/10 (v/v) acetone/water.

13. The method of claim 9, wherein said solution is maintained at a temperature from about 20° C. to about 40° C. in step (e).

14. The method of claim 9, wherein said solution is maintained at a temperature of about 30° C. in step (e).

15. The method of claim 10, wherein said solution is cooled and maintained at a temperature from about 5° C. to about 20° C. in step (f).

16. The method of claim 10, wherein said solution is cooled and maintained at a temperature of about 10° C. in step (f).

17. The method of claim 11, wherein step (g) further comprises washing the second cantharidin preparation with a solvent.

18. The method of claim 17, wherein the solvent used in step (g) is selected from the group consisting of water, acetone, ethanol, methanol, heptane, hexane, pentane, and mixtures thereof.

19. The method of claim 17, wherein the solvent used in step (g) is water.

20. The method of claim 11, further comprising a step (h) of drying the second cantharidin preparation.

* * * * *